United States Patent
Staskawicz et al.

(10) Patent No.: US 6,762,285 B2
(45) Date of Patent: Jul. 13, 2004

(54) BS2 RESISTANCE PROTEIN

(75) Inventors: Brian J. Staskawicz, Castro Valley, CA (US); Douglas Dehlbeck, Castro Valley, CA (US); Thomas H. Tai, Stuttgart, AR (US)

(73) Assignee: The Regents of the University of California, Oakland, CA (US)

( * ) Notice: Subject to any disclaimer, the term of this patent is extended or adjusted under 35 U.S.C. 154(b) by 126 days.

(21) Appl. No.: 09/864,680

(22) Filed: May 24, 2001

(65) Prior Publication Data

US 2002/0012981 A1 Jan. 31, 2002

Related U.S. Application Data

(62) Division of application No. 09/360,186, filed on Jul. 23, 1999, now Pat. No. 6,262,343.
(60) Provisional application No. 60/093,957, filed on Jul. 23, 1998.

(51) Int. Cl.[7] .............................................. C07K 14/415
(52) U.S. Cl. ........................ 530/372; 530/350; 530/370
(58) Field of Search ................................ 530/350, 370, 530/372

(56) References Cited

FOREIGN PATENT DOCUMENTS

| WO | WO 95/28423 | 10/1995 |
|---|---|---|
| WO | WO 98/02545 | 1/1998 |

OTHER PUBLICATIONS

Rommens et al., Intergeneric Transfer and Functional Expression of the Tomato Disease Resistance Gene Pto, *The Plant Cell*, Oct. 1995, pps. 1537–1544, vol. 7, American Society of Plant Physiologists.

Staskawicz et al., "Molecular Genetics of Plant Disease Resistance," *Science*, May 1995, pps. 661–667, vol. 268.

Tai et al., "Expression of the Bs2 Pepper Gene Confers Resistance to Bacterial Spot Disease in Tomato," *Nat'l. Academy of Sciences*, Nov. 1999, pps. 14153–14158, vol. 96.

Tai et al., "High–Resolution Genetics and Physical Mapping of the Region Containing the Bs2 Resistance Gene of Pepper," *Theoretical and Applied Genetics*, Nov. 1999, pps. 1201–1206, vol. 99.

Tai et al., "Molecular Genetic Characterization of the Bs2 Resistance Locus in Pepper," *Diss. Abstr. Int.*, Mar. 1996, p. 4711–B, vol. 56.

Tai et al., "Construction of a Yeast Artificial Chromosome Library of Pepper (*Capsicum annuum L*) and Identification of Clones from the Bs2 Resistance Locus," *Theoretical and Applied Genetics*, Jan. 2000, pps. 112–117, vol. 100.

*Primary Examiner*—Elizabeth F. McElwain
*Assistant Examiner*—Medina A. Ibrahim
(74) *Attorney, Agent, or Firm*—Alston & Bird LLP

(57) ABSTRACT

Bs2 resistance proteins that confer resistance to the plant pathogen *Xanthomonas campestris* are disclosed. These proteins may be expressed in transgenic plants that are otherwise susceptible to infection by this bacterium in order to enhance resistance.

4 Claims, 1 Drawing Sheet

SEQUENCE LISTING

```
<160> NUMBER OF SEQ ID NOS: 14

<210> SEQ ID NO 1
<211> LENGTH: 31491
<212> TYPE: DNA
<213> ORGANISM: Capsicum annuum

<400> SEQUENCE: 1
atgtaaatgt attaccttct ttgcagctca tttcttgaat tagaaaattg ttgttagttg      60
agatgtaata taagcttttt agctctccag aaaatatagt tccaacattt cgaatcgtta     120
gaagttcgaa agatgatata gtacacaata ataaaaataa tagtgcggac actgattctg     180
aaattaatcc cgaaattagt tatgtaaaag aacgaagaag aaaacaaatg gcagtcacga     240
tgcgagtggt atgataaaaa tcattctgga agaaaattgt tatctatgag gaagttgctt     300
gattacatga actccaaaag tgcagccttt ttgcagaaat aaaggaccat ttgtgttcag     360
cattatataa taaggaccta agtgaatcta ctatttaaag ttaagggact atttatgctg     420
ataaattctg cagatatcat ttcaaaactc tttatctttt gttcttatac acataatatt     480
gtcatttctt ctatcatttt ctcaaatatt tcttggagtg aatttgaagt tgtattatct     540
gcaattgaat ggttagtttc ccttaattac tctctcattt aattaaagta taatttgata     600
tagagcaaaa caacacttgt agtagtttat cgaagtctaa tttagctctt tgtactaata     660
gctaaaacta ttcaaaaatg ccgctggttg caagttggat tcttcaaagt tgtgcatttt     720
ttgaggatcc gactcgggtg taacaacttt ttaaagaacc ccagcaacat cctaagaaaa     780
tattacctaa ctaagcagag gcggagccag gattttagtc tatgggctaa aatttcaatt     840 aagggttca atatccgaag gaaaaactag ccaaaggggg ttcaacacac tactatatat     900
atatatatac ataaaaatga ttttaattat gtataaatag tatatttttc catcgaaggg     960
gactcggatg aaacccctag ccaaaggctg ggttctgaac catgacatta tttttcatact   1020 gagcgttaaa ttattttac acattaaatg agctaaagct actgagtttt gccgaatctg    1080
tagctttaag gctggctctg ccccctgtaag aaaggaccag ctgacaatga ttattgcctt   1140
acatgcttat ttgttgtacc tccctgatgc ctctcgatca aaagttgatg ggatttcact    1200
ggaacaaaga aatggacctt aggtctaact caagaggtga ggattgatga agatcataca   1260
```

```
aagaggccaa atgctcttta accctccgat ttcagactca actcactgtt accctgtgat    1320
atctatgact aagacaaata cattacctga tcttatttag tttatgcgtg ccattttagc    1380
aaatctgcgt atctcattat ttgtaatacc attgacctcg tgcaaccctg caggtttcag    1440
gtcatagtcg caaaggacaa aaacgagaat acagtatata tggctcatgc aagtgtggct    1500
tctcttatga gaacaataga atctctcttg acattcaatt cgccgatgca atctctatcc    1560
tgtgatcaca gagaagaact ttgcgctctt cgtgaaaaag ttagttccct ggaagtattt    1620
gtcaagaact ttgagaaaaa caatgttttt ggggaaatga cggattttga agtagaggta    1680
agagaagttg caagtgctgc tgaatacaca attcaactga gactaacagg aactgtactg    1740
ggagaaaata aaagccagaa aaaaaggcg cgtcgaaggt ttcgtcaaag cctgcaacaa    1800
gtagcagagg acatggatca tatctggaaa gagtcgacaa agatccaaga taaggaaaa    1860 caagtatcaa aggaatcatt ggttcatgat ttttcaagtt caacaaacga tattttgaag    1920
gttaagaaca atatggttgg acgtgatgat caaaggaaac agttgttaga agatctgact    1980
agaagctact ctggggaacc caaagtcatc ccgattgtcg ggatgggagg cataggtaaa    2040
acaaccttag caaagaagt ttacaatgat gaatcaattc tatgccgttt tgatgttcat    2100
gcctgggcta ccatatctca acagcacaac aaaaaggaaa ttttgctggg ccttctgcat    2160
tccacaatca aatgatga cagggttaag atgattggtg aagcagagct agcagacatg    2220
ttacagaaaa gtttaaagag aaagaggtac ttaattgtct tggatgatat ctggagttgt    2280
gaagtgtggg atggcgtgag acgatgcttt ccaactgaag acaatgcagg gagtcgaata    2340
ctgttgacta cccgtaatga tgaagtagct tgttatgctg gtgtagagaa ttttctttg    2400 cggatgagct tcatggatca agatgagagt tggagtcttt tcaaaagtgc agcattttca    2460
agtgaagcat taccatatga gttcgagact gttggaaagc aaatcgcaga tgaatgtcac    2520
gggttaccac taactattgt cgtggttgca gggcttctca atctaaaag gacaatagaa    2580 gattggaaaa ctgttgctaa agatgtcaag tcattcgtca caaatgatcc tgatgaacga    2640
tgttcacgtg tgcttgggtt gagttacgat cacttgacaa gcgatctaaa acatgtctt    2700 ctgcatttcg gaattttcc agaagacagt gatattccag tgaagaattt gatgagatca    2760
tggatggctg aggggttcct gaagttggaa atgatttggg aaggagaggt tgagaagtgt    2820
ttgcaagagc ttgtcgatag atgtctagtc ctcgtcagca agagaagtcg agatggaaca    2880
aaaattagat catgtaaggt tcatgatcta atatatgacc tgtgcgtgag agaagttcaa    2940
agggagaaca tttttatcat gaacgacatt gttcttgacg tatcatatcc agaatgttca    3000
tatctctgta tgtataaaat gcagcccttt aagcgcgtga ctggtgatga aattaattat    3060
tgtccctatg gtctttatag ggctcttctt acccctgtaa atcgtcagtt gagagatcat    3120
gacaacaaca atcttttgaa acgaacccat tctgttttct cttttcatct tgagcccttta    3180 tattatgttc tcaaatcaga ggttgttcat ttcaaattac tcaaagtctt ggagctgaga    3240
cacagacaga ttgatggttt ccctcgagag atactaagcc tcatctggtt gaggtaccta    3300
tcattgttca gctatgggaa tttcgatgta cctccagaaa tttgcaggtt atggaatctg    3360
cagacattca ttgttcaacg gtttcgatca gatataataa ttttttgctga ggaaatttgg    3420 gaactaatgc aattaaggca tcttaaactg cccagatttt atttgccaga ttgcccaagt    3480
ggatctgttg acaaaggaag gcacttggat ttttcaaact acaaactat ttcttacttg    3540 tctccacgtt gttgcacgaa ggaggttatt atggggattc agaatgtcaa aaaattagga    3600
```

```
atcagtggaa ataaggatga ctataaaagt tttcgggact ctgggcttcc caacaatctt   3660
gtctatctgc agcaacttga aatattgagt cttatatctg ttgattatag ccttttgcca   3720
gtgatcattt caagtgcaaa agcttttcca gcaacgctca agaagttgaa gttggaaaga   3780
acttatctaa gctggtcata cttggacatc atagctgagt tgcctaacct tgaggtgctg   3840
aagctgatgg atgacgcttg ttgtggtgaa gaatggcatc caattgttat gggatttaat   3900
cgattgaagc ttttgctaat taaatatagt tttctcaagt tctggaaagc cacaaatgac   3960
aattttcctg tccttgagcg cctcatgatt agaagttgca aaaatttgaa agagataccc   4020
attgagtttg cagatataca cacactacag ctgattgagt taagagagtg tcctcccaaa   4080
cttggggaat ctgctgcacg aattcagaaa gaacaagaag acctcggaaa caaccctgtg   4140
gatgttcgta tctcaaatcc atgtaagtat atatttatca aggttatact cagtttctca   4200
ttttcacaag tcaagtcata cacaacagtt atttagcttt gccccatatt ctttcacaaa   4260
aataacttcg acaaaatttg gttaaaaccc tacttaaaat gtaaagaaa ttaacaagaa   4320 tgtcccttat atttgagagt agtaatttta cgaaatgtat cattgtgata catttgaaat   4380
cagatttatc atttccacga tttgtgccta gtttattac tcgtaataat tgaatttgtt   4440
acttcctaaa ataaaaatct tttctgtttt aaatgtatca ctaattatca cgttataaca   4500
tatgtatcac aaatttaaaa atctgggata tgatctaatt taacaaattg ttgaaataaa   4560
gtgttataac gcttaaacat tccgggattt atgtaagtta cccatgtaaa aatgttgcag   4620
caccctgtac tttcgggcta gaatcaagac catcgttcct acgcgtatag acacgaacta   4680
gatgattcct tgttaatata tgtgtgatga tcaatactat agtgttagaa tacctttgaa   4740
tatgaattga ggtcacaaaa atcccctaac tctaagacaa gttgaaaaca tttctaccga   4800
ataagtttta gtgaatgttt aaacttgggt caatttccat tgaccataac ttcttgtata   4860
taatgaatta gaggttctac tatatatcaa atgaaaggtc ttcaaattat ttttccaacg   4920
atactaactt cgcaaaaatt cgatacccga gcgaaaagtt acaaccattt tcgtgaaaga   4980
ggcggtagct gcgcatgatt agcatgcgac gcacgctctg tcgcacacac ctagttttca   5040
ggttctgttt tagtgttttt aagggcaatt tggacccttta cttcacccaa ggtccgtcca   5100
taacataaga ttcacgcccc aagaaagcat aatacactct ataatccaat tttcctctca   5160
aatcaaacca taacccttcc ccaaagatca agatcaagct cttaagtcaa gaatttcaag   5220
aaaacaaatc aagattcagg ttttgttct ttcgaactaa cgtaatctaa ggtatgtggg   5280 gttttctaa aactaacatg ggcattatta aatcgttgca ataatattta aacatggtga   5340
aatcatgagt ttcaaagggg ttttggtaat ttacaatata attgtgtttt aagaactctt   5400
aaataatatt attgctttgg tctttaggcc tttcccccga aattgatttt tgttagtata   5460
tatgtatgta tatgtgattg aagatttgaa atatcaattg agagcatgaa ttattgaatc   5520 tccctctcc cattgtgttt ctacttaaat tgcatgattt aaataatgag tcaagagcat   5580
tattatttat atgaatttta taataattga gatttggaga gggagggaaa tattcatgat   5640
ttaattacta aatgtaataa tttaaggaat tccaggaatg ttttgagaaa ttgaccatca   5700
cttgttggaa ttgttgaaaa gatgagcata tttgcatggt tttgacttgt gttttgaaac   5760
atggaatttt cctatattat ttgaatgata tggtggtctg aattttgtat ttttgaagaa   5820
agagattgta atatgatttt atggcttaga gattcgactt gcaagtcaat ggtatgatga   5880
taccatataa atgtatgcca taacagagta aagagtttcag acttgatttc tcagagaaaa   5940
catgtttaaa gagctaaaag tgggcttaaa gagggttagg tgagctgaaa gtgggcttaa   6000
```

-continued

```
agagggttag gtgagctaaa agtgggctta aagagggtta ggtggttgac cgaagaaggc      6060
ttgagttcaa gttactctta gcctaaaatc atgttttgcc gatacgggta tattattatt      6120
gtacgctggc gacgaccctg tggcgtagta gagattcaga gactccgacc cttgcgacaa      6180
acttgggtta ggggcttggc tgccaagtta acgacagatt ccatatagcc cgtggaattt      6240
cagagttgta gggtatacca cctagcgcag aagtaaaata aagagtatgt cacagatttc      6300
cgtaattgtt tagagtcttt ttaaatatgc ccatgcgttt tcttatcata tttatattta      6360
tgaactattt ttttaaaatg ctcccoctat tttgaataat tttttttatt attttgattg      6420
ctctgcttac attaaattgt attgaccccc ccctttcagg gtctgagctt atctagggtc      6480
cgccaatcgt aaatttccaa caaaacaatt tgcatgtagc ctgttatccc gaaggcttcc      6540
ctaaaaaatt acatttgttt tggtttggtc actggggcct gtcctagatt cagacaagtt      6600
attaatatct tatgtagtaa agatttcgca gactgagaaa ggtgttgtct agatgttgat      6660
aaaattgttt tcgtattgtc ggaccgattt ggtaacatga ccatgttttcc gtctgtttta      6720 tttttataat attttttcttt gttatttgag tattgtgcat gattaccaga atgtagaagg      6780
gcgcccggcc cttcatgatt cgagatgctt gttatggcca gggtctcggc tcgggttgtg      6840
acaaacttga tatcagagca cggtccatgg tcccagggtg tctgcgaaat cgtgtctagt      6900
agattcttgc ttatgggtgt gttgtgcacc acacttataa tccggaggct accgggcatt      6960
taggagttgt ttctcattct ttcatactcc agttcgtgct atagagtcgt ccataagaaa      7020
gatatccaag ttcattcctc gttctaattt catggacatg cctcactgtc gaggcaatac      7080
aagtcctaag agtctagctt cccactgatg tggttctctt tgattggttt atccacaaag      7140
ttatgagata gcatgtggac gggagaggag tccattagtg ctgcaaggta tattgatttg      7200
tgtgtatgcc ttcatcctga tgaaatcgtt ctttccgacc tgaggtatga actgtattca      7260 ggctcctttta aagaaattc tcgtagggga tgtgatgctt aaggataatg atatgtgaca      7320
caatgttgga accgtctctc ctcccgaata gttatatatg ttaaagtgtc atgacctatt      7380
ggtagtgaga tggtctggaa gttggtgaca tgaattcaca aggttaacag tcagagtgag      7440
ggtgatattt gtgtaaataa agagttttag ttgtatagtc gtggattaag gagtgggttg      7500
ccattgtata ttgatagact aatgtgttat aatgatagac tagtgtgcag taatatttgt      7560
agattgtatg gtggtctgtg aagaaagatg caggatatga ttattattta ttcagaatag      7620
ggaaggatca tggaatggat ggttatagtg gttgtagaaa tcatttataa gctgtgaatg      7680
gaaaggagta gattagttaa taagttgtaa gtagagactc attagtgttt attgaatttt      7740
gaagatcact gtgatgtaca attaacatgt atgacgtgag aaattagaat atattgataa      7800
gattataatg ggttatattg caagattaag atgactaaac aaatgatgtg acttaaccct      7860
ttgatggtct ttctttagta gtgaatttga gtgtatcgtg ggatatggcg ggttgtgctg      7920
aagtagtagc taagtgaagt gaagtatttg gagttgattt cccaatttga tggactagaa      7980
tagtatgtgg catgcttcgt tggtggtaca tgattgacgc tagatagtat aggcttgaac      8040
ttgagatgtg aagtgtggtg gtaagggtag tagcttaagg agtaatgatg catgttttgt      8100
ggattaatta gtaggcttgg tgtgatgtgt gaaatggcct aaattaatga tttatgaaaa      8160
gtttaagtgg taattgtcac accacttttt ttcactccca aaaagaatta atttttaagt      8220
ttcgaaaggg ttttattatt aaagtgacaa aagatgaaag ttgtttcaaa aaaggattca      8280
ttagtttcaa aactcagagt caccacttgg cataaatcaa gtgtgccaag tcacccgtgg      8340
```

```
atatccttttt tcaaaacggt tttgactcta taaaaactga tccgcgaaca gagatttcgg    8400
ctaaggaatt ctgttgatcg aggagaaggt gttaggcacc cctcgatccc gtggttcgac    8460
cacggtcgct tggtggagta tatcggctaa tttggacagt atgaatgtat aaaccacacc    8520
aaacataaat aagacgattc aatcaagcaa acaaattcaa aaataatgtc cagtctaatt    8580
ataagtccaa aatagaaaaa gaatgcgaaa atataaatcc tattctaccc tacactaatt    8640
ttatactacg ctcctatcca cccgatgcct cgagccttca tcacggacgt cctgcaaata    8700
caaaatactt cggggaatta cccgacgaat aaatacaagt gatctcgtgg cattccccga    8760
ttaaatgaat acatttccca aatgcaagaa ctaaaaccaa accgttcaac tcgaattcca    8820
cattcaaaca ttcaacaaaa aaacttattc ctaaatttttt gcctacccga accaacattc    8880
gcctatccat ttcaacgtac cataattttta tcacattcca acaatattca tgctcattac    8940
gaattaaaca aaacaataat aaaccaaagc taatctaaat tcaacttttt ttatcaattt    9000
ctcaatttca tccccaaat ccatttttaa ccacattatt aaaccagttt gactatcaaa    9060
tcacttttca aaatccgaaa ctaacaacac atacccaac gatgattcaa acatttaagc    9120
ataccaatca ttcatatcca caacaacaat taacattttg ctcgaaatat tcaaaactgc    9180
actacaaaat cacgatatta accaacttcg atataataaa aaagtggagt tgagagatgg    9240
acctttgaag aatcgatttc gttgataata aaatcaagaa acccggact atagaattcc    9300 taataggacc tcagcaatga cgaactccaa ctctgtattg aaaaatttga gatccaaaac    9360
tgaaactccg taaatccaat cgaacccaaa aacctacact gttcatgtac tattcacgat    9420
actgttcaca acactgttca cggtattgtt cacaatactg ttcatgacac tgttcacgac    9480
actgttcaat gatactgttt ctctctcaat ttttcctcgc gcgattctct cctctcgctc    9540 ggttttttt gttcttcttg tgaggaagat gatttgatga ttgttgttat tgtggagaag    9600
atgatgatga aagaatgagc ctcccctttt tttcattttta gaattttcct tttatatttt    9660
ttatttgttt ttttttcctttt atttattatc ctatgtgaaa gcatataatt ggtggctttt    9720
gggaataatt gtgtggcatg tggaaaagtt agtgtggcat gtggaaaaat gagggtgaca    9780
tgtggaaaaa tgattagggc gtgtgccttt tgcatgtatg taatgaaaaa tggaaagtga    9840
ggtgttgagg tggcatagtg acgtggcaaa gatgcatgta tctaattatt ttcaattttt    9900
tttttttttt tgggggggg ggagaaatta tcaattaaat aaaagtatga taaggtgata    9960
gaataaaaat aaaaataaaa ataaaacaaa tgattaaaat attttcggga aaggacaaaa    10020
ttaacatgtc taacatcatg cccccttttgg atgtaaacaa catggtgttt tcatacaaag    10080
cagtagacaa tgagacagaa ttttgtcttg acctttattc aaaagcacgg agcacgagga    10140
aggagggaaa acaggtcttg acttaggaca tcctacctac ccaagttatg agggaattaa    10200
gtgacagtta tctcaaagga ttggtaggag atggactatg ccgagttgga gagtcgagtg    10260
aggtcccatc gaggttccga tctgtggctc tgttattaca tcaaaaataa aaattacaag    10320
ttaaaaacat aaatgaaatt acaaaatcct atcttcgcag cttctgttgg actcttgact    10380
tgagtttcat caccctattc ttcaggcggg cttctgattt gaaatttctt caacttgttg    10440
cttggttttt aatttcatca ccctgttctc caggcgggct cctgacttgc tattttcgat    10500
ctgttgactt tcatttttctt cactttgtta cttgactttc aacttcttta ccttgttgct    10560
tgactttcaa tttcttcacc ttactactta actttccatt tattcgccct gtgcttcggg    10620
cgggctcctg aaatcacatt aaaactagaa agaaaattat cccaaacaaa attattgtaa    10680
agagaaaatt gtttgccaaa aaagtaaagt tccaaaatag atactgttttt tttttgcccc    10740
```

```
agtttaccat caaaagactt ttgagaaagt cagatcatac ctacttgaca taatgaatca   10800
agactctgat caagaaatgc atctcttaac aataaaattg aatgaccaag actaggaagt   10860
gcgtctccta agaattaaag tgaggaattc tgactagaaa gtgtgttttc tagagataga   10920
agtttaaatt aaaagtgtg tcacctgaca atgaaaact  aacaagaag tgcgtctcat    10980
aaggattaag tgcaatgact cgactagaaa gtgcattttc tagaaatcaa ggagaatgac   11040
tcaactaaaa ggtacgtctt ataggaatca aaggaaatga ctcgactaaa aggtacgtct   11100
tctaggggtc aaggggaatg actcgactaa aaggtacgtt ttctaggggt caaggggaat   11160
gactcgacta aaaggtatac cttataggaa tcaaggggag atgaatcaac taaaaagtac   11220
gtcttatagg aatcaaggag gatgactcga ctaaaaggta cgtcttatag gaataaaggg   11280
ggatgactcg actaaaaggt acatcttata ggaatcaaag aaagatgact cgactaaaag   11340
ttacgtctta taggaatcaa agggagatga ctcgactaaa aggtacgtct tataggaatt   11400
cagggaaatg tctcgactaa aaggtacgtc ttctagggt caagggaat  gactcgacta   11460
aaggtatgc cttataggaa tcaagggggc tgactctact aaaatgtacg tcttataggaa   11520
atcaaggggg atgactcaac taaaaggtat gtcttccaag agtcaaaggg aatgactaga   11580
ttagagggta cgtcttctag gagtgaaggt tcaatttaag aagtgtatca ctcgaaaaat   11640
gaaaactaaa atcccctgat aggaaagtgt gtctccgagg gatataagat gatgaatttt   11700
taccatgatt taattatcaa acatgtgcag caacattgct tcctgcattt gtaaaagcga   11760
gaaattaggg gccttgatgt ttaggctttg aaatccttga tttgaaggtg acatgtgttc   11820
ctgtttcatg taaagaaaaa ttgtgagttt aaaaacatgg aggcaggttt gtggctttgg   11880
ctttcgtggc aaacgctctt gccgtcatca catttaacct tgcttccaac cattacatat   11940
atcattgact tgatgcatca ttgaccaaac tcagattatt aagagtgact gagacaaaca   12000
catcatctct gctttgtcat gcttctcaga tagacccctt gtaaccttgg tatttcatga   12060
gttttcagac ttctctattg acaatacttc tacatacccct ttttggctca caattatgtc   12120
tctttcatgt gctagctttt gtcttgcttt gtgcaattaa tgaagctagt agctagtttt   12180
ggaatctttc ctcacttgtt ttgacacaca cttgactcaa agacaagaaa agaaaataga   12240
atgcaatttt ttatttggat aactgactca agataaaaca aaaataaaga gaagaaagaa   12300
aagacaatga atgtctacgt ttgaaacaaa gaaatgacaa atttatcgaa aaacgacag    12360
tcaactctaa tgattatgcc atgcattttg gattgagcag cttgatcttt tcatccaaac   12420
tttctaccaa ttgttgttga gttaacggcc ttgaaactga gttacttcct taggtcaatt   12480
gcatttacga cctcattcgg ctagtggcgc cttgaagggt tttcgccaac aagcctctct   12540
catttttctc tcagctcact atcgtcttac ggtgcccgta agggttttca ccaataagac   12600
tcacatttttt atttctctcc tgacttttta tgttgaggaa acaagtagt tccccaaatg    12660
tgtcatcata cccattgcat gcttagcctt agcattctca gagattgatc tgaaggtctt   12720
tctttggttg taacttggct tttggataag gttagaaaga aaggatgaca tgaggcccaa   12780
acaacacttg aagtggggta agacatatag cttttgaaat cgactcaaac aatgagtatt   12840
aactcatgcc ccagtttctt cggactgggt gactctaaat tatttatttg gctggaccga   12900
gctccggtaa gacagcctac atattcaccc tcgaaagaga gagtcaggtc atgcgtagtt   12960
ccgtcagctt attctttcac ttgattctaa aattttctct tttgttgact cttttctcttt   13020
gggaattttc taactttatt tttcttgaca cttttctctt tttttttcttt ggggacaaaa    13080
```

```
tttcctttc  tctcttctt  tttttttttg  aaacttttct  gacactattt  ttttcgacac   13140 ttttctttg  agctttgatg  actctatctt  aattccaaag  gaggtgtatg  aaagaagata   13200
aaataaatgg  ggtaaataaa  ggatgacaca  atgtttggat  agcagaatga  aatgccttca   13260
tcatatcaat  ccttgagaat  gcaagtacat  aacatgcaat  tggaaaatgg  gagataaaga   13320
tcatgtgtaa  cattttaaca  acactaactt  aaactgaaca  tgtgtgccac  ttcttcttct   13380
tctatacttg  tccaacatac  accaccacct  ttgttatgca  tccctcacat  cgaatgattc   13440
atgttttcgt  ggagctgatt  tcttttttgtt  cctcttgata  taggatcccg  cagccactgg   13500
ttgacctaat  tgagacatgt  ctttcaattg  atggccgagt  tattcttgtg  attcctaaaa   13560
tatttgtctt  aattttcaga  aaaggcttca  acttgtcacc  aaatgtctca  gcactctatc   13620
tattttctta  gatgtttctt  ccgaccttag  ccctctaatt  tcacgttcat  gcttaaacta   13680
gattttaaga  tctgactgaa  aatttcacta  gtatgtcata  tcactagagt  caacataaaa   13740
tgtactatgt  aaaaaaaaca  aacaaacaac  acatgtttaa  aacacaaata  aaaatgggac   13800
atttatttta  gttgaaaaga  tagaaaggtt  tgaacataag  cgacaaaagg  actaaacaag   13860
atagatccca  aactcaccc  tgaaataatt  cggacaacag  aaaatgaaac  aaaacaagct   13920
accagacctc  ttcttattag  ggagaggagt  gacttctcaa  ttgctcatcc  tgacatcaga   13980
gctttcctca  ctatcaatgt  tctgcaccat  aatcaatttg  tcttgaatcc  tctgttcaat   14040 ttctctttt  aaagcacgac  aatattcaat  actgtgaccc  tgaacatcag  aataatatgc   14100
tcatcgtaca  ttaagatcaa  aacttcttga  atgtaggtca  ggagtatacc  caaggagagg   14160
agtgatcatg  ccctgctgta  ccaatctctg  gaataaactg  gcataggatt  ccccaatagg   14220
agtgaaatta  tcttttttcct  tcctcctctt  tgcgatctct  ggcctcggat  gaaacttgga   14280
tttagaggtt  ccttgataaa  tttgtggggg  tcgaggacga  tgttgaggga  caggtgcatg   14340
ccattgtgga  taataagatg  gatgagcata  caattgtgca  ttgttcaaag  gatattgagg   14400
aagtggaatg  ggatttcttg  gattttgagg  aaagaaacct  tgttgcaagt  ggttatgtgg   14460
atctaatatg  taagctcggg  attgaggctg  acagtattgg  tgggttggac  ctctcaaact   14520
ttgctttggc  cctggcacga  caataggtgt  gttttctttc  tactttcctt  tagtttccct   14580
tggttgattg  caatgtcgtc  ccaaatgttt  cacagaatcc  ttctgtccat  caggctcccc   14640
aaattttgat  gtcttaaagc  tggcagaaag  gttaacactt  gaagacatgc  cccagttttt   14700
atatgaaaca  tcttcatagc  ccatacggcc  aggggaattt  ttcatatcat  tttctacact   14760
cttaactttc  ccaaccactt  tctctagctc  ttctagcatg  ctaggcttct  tagtaagaaa   14820
ttttggcggt  ccacttaatt  taacagtagg  ctcaatagta  taacaataat  catcaagagt   14880
attgaacgtg  gattcactag  tggactggag  aagcacaatc  gttggattga  tagccaaagt   14940
gaagaaaatc  tttttaaatt  ctgaaccaac  aataggctgc  ctatgtatct  cacatcccga   15000 aagagggaa  tttggggtac  gtagttcgtc  cagattggaa  aattaaggat  tatagaacaa   15060
acaaaacctt  gacttgagag  acacaactgc  aggatgaaaa  taaatctttt  tgggttttt   15120 aatttgacac  ttcatacaaa  aatgacatca  acaactatga  aagaaaaatc  ttttggtatt   15180
ttcgttatac  gaaatgtaaa  aaatttctaa  catcttttt  tgcattttc  ttttataaaa   15240 actcctatga  atgaaatttt  attttttga  agttttcgaa  ttgtgaatgc  atgctaaacg   15300
agacaaagga  aatttttttt  gatgttttg  agaaatgag  tgtgaaggt  aagaaaaatt   15360 tttttcaatt  tttgaattgt  ggaaaaccaa  agccataaaa  aactttaaaa  actatgaaac   15420
tttttttttt  tcttttcgac  tcaacaacaa  caaacccagt  gtattcccac  ctagtgggt   15480
```

```
ctgggggggg gtaagatgta cgcagtccat acctctacct ctaaagaagt agaaaggctg    15540
tttccgatag atccccggct caagacacga gacaccacac aaatacatag taaagcacag    15600
aacaagattt cataacataa atacggcacc cataagtaat agaaaacaga ggaaagcacc    15660
cagattcgta ataaaacatg gaacacggaa tcataacaag aataataccc ccaccaagta    15720
attccctata ctagcgaccc aaactggccc tagtcttctg ccctaattcg cgtcctccag    15780
accttcctat ctagggtcat gtcctcggtg agctgtaact gctccatgtc ccgcctaatc    15840
acctcacccc agtacttctt cggcctaccc ctaccccgcc taaaaccatc caacgctagc    15900
atctcacacc tacgaaccgg ggcatccatg cccctcctct tcacgtgtcc gaaccatctc    15960
aatcagactt cccgcatctt gcactccact ggagtcacac caaccttctc tctgatagtc    16020
tcattccgaa ctctatcccc tctagtcatc ccacacatcc agcgcaacat ccgtatttcc    16080
gccaccttca tttttggat gtgggagttc ttaactggcc aacactccgc tccatacaac    16140
atggccggac ggactaccac cctgtagaat ttgcctttaa gcttggacga cacctttta    16200 tcacacaata cccccgacgc gagcttccac ttcatccatc ccgccccaat acggtgcgat    16260
atatcctcgt caatctcacc gttaccctag atcacggacc cgagatactt gaaactatcc    16320
ctcttacata cctcctgtga ttccagcttc actaccacct cattctccag cctcacgtca    16380
ttaaacttgc attccaaata ctctgtcttg cttctgctca acctgaaccc tttagactca    16440
agagtttggc tccacacctc tattgtcatt caccccctcga ttctcgtcaa tcagaataca    16500
tcgtctgcaa aaagcataca ccaaggcacc tcccctttgaa caattctttt tgactcactt    16560
gttctatttt tttcaacaat tcttgcctac gcccttact tctaacacat gcttttccca    16620
aatcagttcg tgggtttggg ccattttctc actgcttcaa ctctctgggg atccactctt    16680
atcccgtcac tggacacaat atgccccagg agggcaataa cgtctaacca gaattcatac    16740
ttagaaaagt tggcataaag ttgatgatcc ttaaaggtct gcaggataat tcggaggtga    16800
ttggtgtgat cctctttact cttagaatag atcagaatat catcaataaa tacaatgacg    16860
aacaagtcaa gaaactgacg gaacactcta ttcataagat ccataaaggc tgcaggggcg    16920
ttagtcaacc cgaaggacat gactagaaat tcatggcgac catatcgggt tcggaaggct    16980
gtcttgggta tgtctgactc cctaattttc aactaatgat aacccgaacg aaggtctatt    17040
tttgaaaagc acttagcacc ctgaagctgg tcaaaaaggt cgtcaatcct aggaatagga    17100
tatttatttt taatcatgac cttattcaac tgacggtagt ttatgcacat ccgaagggac    17160
ccatccttct ttcgcacgaa gaacacaggt gcaccccatg gggaaacact aggacgaata    17220 aaaccttttgt ctaggaggtc tgcaagttgt ccttttaact cctttagttc cgcgggagcc    17280
attctatatg gcggaataga aataggacaa gtgtctggca acacatcaat gccaaaatct    17340
atctccctat caggggtat ccctgggaga tcttcgggaa agacttctgg gaattcattc    17400 acaatagga ctgactgcag aggaaagttt ccaacttttg aatctttac ttagacttga    17460 tgatacatac aaccatcgga gataagcttt cgggctctaa gataagagat aaagtgacct    17520
ctaggttcca cagaactccc tgcccataca actggtgtct cattcaggaa agaaaaagtg    17580 accttttcggg ttctgcaatc aaggatggca taacatgaat ggagccagtc catcccaaga    17640
atgacatcaa aatctatcat atccagttct ataaggtctg ccacagtttt cctactatga    17700
atagacacga cataatttct atatacccctt ctagcaacaa cagaatcacc tacaagagta    17760
gaaacagaga agggttctac aataacttcg ggctcaaacc caaaaccaac agccacataa    17820
```

-continued

```
gggttcacat aagataaagt agacccggga tcaagcaata cataaatatc atgagaaaag    17880
attcgtaaca tatgggtgac aacatttggt gaagcttttg cctcctggca gttagtcaaa    17940
gaatataact ggttgcgacc acttccggca gctgaagggg cacccttagg aaaaggagtt    18000
gtggaggcgg cttgggactt atccccccccc ccccccgca ttactccagc aaatgggcaa    18060
tctctctgaa ggtgacccac tttgccacaa gtatagtagt ttctcccttc aatccagcac    18120
ttccctaggt gattccttcc gcaaacctca caccgcggat gagtacgacg ctgctgggcc    18180
atattgccct gtgactgtgt acctagagct ttggaaccat gaggagtctg gaaactctga    18240
gtttgtctgt ttgtcggtgg tctgggtgct ggggcactgt ttgctgactg tgcattattc    18300
caatacttct tcttcgacca cttattaccc cagttaccac tctgcggctg actcttgtgt    18360
tggtccgcag atctagctct cttagcttgt tggtctttct ctgtagattc agcaatcttt    18420
ttcttcttct cttccacttg atgcatatga acggtcagtc gagcaaagtc taactcctta    18480
ttcaacatag cccctggca ctcaagtacc aggtcatcag caaggccaga tgcaaatttc    18540
ctcatccggg ccctcatatt actagtcaac tctggtgcat aacgggctag tttattaaac    18600
ttcaaagtgt actcctggac actcatactg ccctgcttca gattcataaa ctcttctgtt    18660
ttggcctcct tcaactccag aggaaagaat caatcaagga aagcttccac aaattcgccc    18720
caaactgtgg gctcagcact ttcacatttt tcatcttccc agtcggcata ccactgactc    18780
gcaacatcct tgagctgata ggttgctaac tccacccctt caacctcatc cacacgcatc    18840
accttaaaga tcttttccat ctcatccatg aaatgaactc ctgtggatct tcctctactt    18900
tggtgccagt gaacttaggt gggttcattt tcatgaaatg ttcgactcta gtagcctcaa    18960
atgtaacaga tgcagaccta atatctttcg atcgttgagc ctggttagct accaactgtg    19020
ccagcatatg aatagaccgt ctgaattcta catttgaaat atctccctga gcagttgggg    19080
gacggttggc attagtccac ggagcctgag gtggactggt cgggactaga gggactcccg    19140
gagtagggat aaattttgaa gtgtgagccc tgttacgggt ctgcatcgca tgggtgggac    19200
gggcctcatc tgcttgagca ttttgatcga cgataagacg tggaggcata aatgtgtttc    19260
tgaaacacaa gggatcattg attaggggac agttcggact ctgaagcatg aactaaatca    19320
caaagaaggg aaacatttcc taaacgctta gcagcctcct acttataagt gtggcgtgct    19380
acacacccat aaacaagact ctacctaacg cgatttcgca gacaccctgg gaccatgaat    19440
cgtgctctga tactaagttt ttcacgaccc gaaccagggc ctggccgtga cgagcatttt    19500
gaaccatgga ggcccgaaac accattatct gtctggtaat catgcaccta attcatatga    19560
tcaaagtaat gcggaagaaa cacaatataa cagaaacatg gtcaagaatc atatgaaagc    19620
gataatgggg aatagtgtcc cacaatctaa atcaacatct ctaaaatcgt ccgcgaaatc    19680
tctactacat gactgaaaca atgtctattt gaaaactggg acaaggcccc cagcagaccc    19740
taaaactgaa tatattagat aaaaggactg caggatataa gaccttctga agcatagaag    19800
gctcaccact tgtctccgca actctgtctg aataatctac tgattctctt gaccectaga    19860
ctgggcctct gaacctgaga ggttggagag aggaggggggt cagcataaag gtactggcac    19920
gcagagatat caaagcaaaa cataatattt ttacaaaata tagttgagag ccattataaa    19980
gcaatttcgt atcaaatcat ttgaaagaac atgggtgtaa tgcaatagtt tttctcaaca    20040
ataatgaaat gcaactgagc taggtggaat accctgcata atttacacca actgtcaaac    20100
ctcggttgcc gccaagatta gagtataagt gagggagaga cacacaagat cacacaacat    20160
ggagtctcga cccaatggca gtgcccaaaa taacttggct cggggttccta cctatagtcc    20220
```

```
caatttggga atgacatgaa gtcaagtgca caagatcact tagcctggta ccaatattcc   20280
gtatcggcaa acacgttttt ccagcgatta gcccttttgt ctcaaacgcc ttcttcgggc   20340
atccaccttt ctcatgtaaa atcaatgcat tcaaatttca tcttattcaa tgacatgtcg   20400
tattttgtcg ggtatcgtca tacccgactt tcaagtcatc aatatcacat ccacatatgc   20460
ataatcacat aaaaaccaag gtgcttcatc atttacaagt ggtgaacaat atttttcaa    20520
attcatgctc tcttttgttg atcacaatac aatatggagt atcgaaacat tatcatgaga   20580
atttgaaaac aatttatcat tcatatttat caaacttcca tggaaaatct caaatcacat   20640
atgcatggtt gcaaccattg aagtatatag gcaaacaatt cccatgacat aaagaaaacg   20700
acttagaaat cgtattgaaa gcaagatatt agcatttgat tgaaaacccc catttaaaag   20760
catgcatgtt cataaaaact acacccatga gattttttgga taaccccacg tacctctatt   20820
tccaaggata atagatgttt cttgaagctt gcggattgtt gattccaaat atgtaattat   20880
cttttgaaaat ctacggtcaa atcttgaact atttgggttt ttattttgaa accctaagga   20940
gaatcttgag cacttttgat gaagaatat gtattttggg gttcttggaa ctaaatctcg    21000
tgttacggct aagtaagggt ggaaaaggac cactttgtcc tcaacatgga gtgtttaaat   21060
caccagaatt ccttacatag gcgccgccca tcccgttgcc tatgttcaca taggcgtcgc   21120
ctaggctatt gcctatgcat tccagtggcc atgggcgatt ggttaggcga cgcttatcac   21180
tttgaagggc cataacttct tgtcgggtgt cggattttag ccaaattggt atcattggaa   21240
agctaactcg aatacctatc atttgacaaa tagtaggctt tctaattcga catatacata   21300
gagttatggt cgatggaagc tgacacactt tacaacgacc ataaaactta gtcgatcgaa   21360
atagtttcaa ctcgtccttg agttgaagga cctctatggt cttatttcaa gcttgagtgg   21420
attcacatgc tacgcaataa ttaacatgtc gtattatcat gggattttat ggcttcggga   21480
ttagcaatgc ttcaaaatca tggtctatat tgtagcccga attgtggggc gttacattat   21540
cccccccttag gatcattcgt ccctgaatga tgatgcggga cacagacaga cattatttca   21600
agcataataa aggactagga aagataagat aggaatagta ccttctatct cctccttcat   21660
cgaagcaaac aaaattggga atctaattct catgtcatat tctgactccc aagttgcttc   21720
ttcgactttt tgattcctcc acagtacctt tactgaggct atctctttgc tcctcagctt   21780
tcgaacttgg cgatctaaaa tttcaacggg ctcttcttcg taagacaagc agtctgtcac   21840
tttgataccc tctactggca ataccgtaga atgatctcca atgcatttct tcaacgtaga   21900
tacatggaat accggatgaa cggaacccaa acttgcaggc aattctaact catatgcaac   21960
tgtaccaatc ttcttcaaaa tctgatatgg ccctaataac gagggctcaa tttacccctt   22020
tttccaaatc gcataactcc tttcatagga gaaaccttga gaaacaccca atcaccaatt   22080
tcaaactcta gttctcttct ccgaacatcg gcataggaca tctaacgact ttgagcagtc   22140
ttgactcgtc tctaatgatt ttcactttct ccatcgcctt atgaacaaga ttaggcccat   22200
acaactgagt ctcacccact tcataccatc ctatcggaga cctatatctc ctccaataca   22260
aagcctcaaa aggagccatc ttgatgctgg catggtagtt attattgtaa gcgaattcaa   22320
ccagtggcag gtgatctacc caactacctt tgaaatcaat tacgcatgcc ctaaacatat   22380
cttcgagggt ctgaatggta cgctcagctt gtccatccgt ctgagggtgg aaacctgtgc   22440
tcaaattcac ttgtgtacct aaacccttct gaaaggatct ccaaaactga gatgaaaact   22500
gcgtacctct atcggatata atagacattg gtgccccatg caatcgaact atctcctcaa   22560
```

```
tgtaaatctt agaataaacc tctcccaaat aattagtcct cacaggaaaa aagtaggctg    22620
acttggtcaa ccgatctaca atcgcccata tagaatcata ctggtttcgg gatctcggaa    22680
gtcctgtaat gaagtccatg tttatcatat cccacttcca taaaggcagg gctatctctt    22740
gggaagtacc acctggcctc atgtgttcta ccttcatttg ttgacagttc aaacacttgg    22800
acacaaaatc agctacatca cgtttcatgt tattccacca atacaaggtt tttagatcat    22860
ggtacatctt agtagagcct gggtgaatga catacctcaa agtgtgcgcc tcattaagga    22920
ttctttctcg tatcccatcg acattcgaaa cgcacaacct accctgaaat ctcagaatac    22980
tatcgccact aatttcaaat gacataacca tttgttgacc cacatctttc ttgattttca    23040
tcaagatggg atcttcaacc tgcttctcct taacttcagc acaaagagat gacttagcta    23100
actcatgaac aatcacccct ccatcttcgg aatctaagag tcgcactccc atatttgcaa    23160
ggcggtgaat atccttcacc atctctttct ttccttcttc tacataagaa aggctgccca    23220
tagaaaacct actgagggcg tcggctacaa tatttgcctt gcccggatgg taatgcagac    23280
tcatatcata gtcttcaaa agctctatcc aacgcctctg cctaaggttt aattctttct    23340
gtgagaaaac atactgtaaa ctcttatggt cagtataaat atcaacatgc actccataga    23400
gatagtgcct ccagattcta agtacaaaca ccacggctgc taactccaag tcatgagtag    23460
ggtaatcgca ctcatgcacc tttaactgcc tagatgcata agctatcacc ttaccacgct    23520
tcatcaatac acaaccaagt cccatacggg acacatcaca ataaaccaca aaattatcta    23580
caccctcggg aagggtcaaa acaagagcag tagccagctt gtccttcaat ttctcaaaac    23640
tgttttcaca caagtcagac cactcaaact tcatcttttt ttgagtcagt ttagtaagcg    23700
gagaagctat ggaagaaaaa cttctacga accttctgta ataccccgcc aaacccaaaa    23760
agcttcaaat atcggttgga gtcgtgggtc taggcctttt tctcactact tcaactttct    23820
agggatccac tcttattccg tcactggaca caatatgccc caggaagtca atagcgtata    23880
accagaattt acacttagaa aatttggcat atagttgata atccttaagg gtctgaagga    23940
taattcggag gtgattggtg tgatcctctt tactcttaga atagatcaga atattatcaa    24000
taaatacaat gacgaacaag tcaataaatt gacggaacac tctactcata agatccatga    24060
aggctgcagg ggcgttactc aacccgaagg acatgactaa aaatttgtag tgaccatatc    24120
gggttcggaa ggctgtcttg ggtatgtctg actccctaat tttcaactga tggtaacccg    24180
aacgaaggtc tattttttgaa aagcacttag caccctgaag ctggtcaaaa aggtcatcaa    24240
tcctaggaag aggatattta ttttttaatca tgatcttatt caactgacgg tagtctatgc    24300
acatccgaag ggacccatcc ttctttcgca cgaagagcac gggtgtaccc catgggaaa    24360 cagtaggacg aataaaacct ttgtctagga ggtctgctag ctgttccttt aactccttta    24420
gttccgcggg agccattcta tatggcggaa tagaaatagg atgagtgtct ggcaacacat    24480
caatgccaaa atctatctcc tatcaggggt attcctggga gatcttcggg aaagacttct    24540
gggaattcat tcactacagg gactgactgc agtggaaagt ttccaacttt tgaatctttt    24600
cctcggatta gatgatacat acaaccatcg gagataagct ttcgggctct aagataagag    24660
ataaagtgac ctctaggttc cacagaactc cctgcctata caactggtgt ctcattcggg    24720
aaagaaaaag tgacctttca ggttctgcaa tcaaggatgg cataatatga atggagccag    24780
tccatcccaa ggatgacatc aaaatctatc atatccagtt ctataaggtc tgccacagtt    24840
tccctactat gaatagacac gacacaattt ctatatatccc ttctagcaac aacagaatca    24900
cctacaagag tagaaataga gaagggttct acaataactt cgggctcaaa cacaaaaacca    24960
```

-continued

```
acagccacat aagggttcac ataagataaa gtagacccgg gatcaagcaa tacataaata     25020
tcatgagaaa agattcgtaa cataccggtg acaacatctg gtgaagcttc cgcctcctgg     25080
cggttagtca aagaatataa ccggttgcga ccacttccgg tagctgacgg ggcaccctta     25140
ggaaaaggag ctgtggaggc ggcttcggac ttagccccc tcccccctc cccgcattta      25200 ctccagcaga tggacaatct ctctgaaggt tactcacttt gcaataagta tagcagtttc     25260
tcccctcaaa ccagcacttc cctagatgat tccttctgca aacctcacac catggacgag     25320
tacgacgctg ctaggccaca ctgccctgag actgtgtacc tagagctttg gacctatgag     25380
gagtctggaa actctgagtt tgtctgtctg tcggtggtct gggtgctggg gcgctggcta     25440
ctgactatgc attattccaa aacttcttct tcttcgacca cttattaccc cagttatcac     25500
tctgcggctg actctggtgt tggtccgcag atctagctct cttagcctat ctgtctttct     25560
ctctagattc aacaatcttt ttcttcttct cttccacttg atgcatatga acggttagtc     25620
gagcaaagtc taactcctta ttcaacatag cccccggcac tcaagtacca ggtcatcagc     25680
aggccagatg caaatttcct catccgggcc ctcatattac tagtcaattc tggtgcatag     25740
cgggctagtt tattaaactt caaagtgtac tcctaggcac tcatactgcc ctacttcaga     25800
ttcataaact cttccgcttt ggcctccctc aactccagag gaaagaatcg atcaaggaaa     25860
gcttccacaa attcgcccca aactgtgggc tcagcacttt caccttttc atcttcccag      25920 tcggcatacc actgactcgc aacgtccttg agctaatagg ttgctaactc caccccttca     25980
acctcatcca catgcatcac cttaaagatc ttttccatct catccacgaa ctcctgtgga     26040
tcttcctcca ccttggtgta agtgaactta ggtgggttca tcttcatgaa atgtccgact     26100
ctagtagcct cagatgtaac agatgcagac ccaacatctt ccgattgttg agcctggttt     26160
gctaccaact gtgccagcat atgaatagat catctgaatt ctgcatttga aatatctccc     26220
tgagcagttg gaggacggtt ggcattagtc cgcggagcct gaggtggact ggtcgggact     26280
ggagggactc ccggagtagg gacaaattcc ggagtgtgag ccctgttaca ggtcctcatc     26340
ttcctgagca ttctgattga cgatacgacg tggaggcata attgtgtttc tgaaacacaa     26400
gggatcattg attaggggac agttcagact ctgaagcacg aactaaatca cagagtaggg     26460
aaacatttcc taaatgccta gcagcctcct gcttataagt gtggcgcgct acacacccat     26520
aaacaagact ctacctgacg cgatttcgaa gacaccctgg gaccaggaac cgtgctctga     26580
taccaagttt ctcatgaccc gaaccagggc ctgaccgtga cgagcatttc gaaccatgga     26640
ggactgaaac acccctatct atctggtaat catgcaccta attcatatga tcaaagtaat     26700
gcggaagaaa cacaatataa caaaaacatg gtcaagaatc atatgaaagc gaaaataggg     26760
aatagtgtcc cacaatctaa atcaacatct ctaaaatcgt ccgtgaaatc tctactacat     26820
gactgaaaca atgtctatct aaaattcggg acaaggcccc cagcaaaccc taaaactaaa     26880
tataagataa aaggactgca ggacataaca ccttccgaaa cattgaaggc tcaccacttg     26940
tctccgaaac tctgtctgaa taatctactg attctcttga cccctagact gggcttctga     27000
acctgagagg ttggagaggg gaggggtca gcataaaggt actggcacgc agagatatca     27060
aagcaaaaca taatattttt acaaaatata gttgagagcc attataaagc aatttcgtat     27120
caaatcattt gaaagcacat gggtgtaatg caatagtttt tctcaacaat aatgaaatgc     27180
aactgagcta ggtggaatac cctacataat ttacaccaac tgtcaaacct cggttgccgc     27240
cgatattaga gtataaatga gggagagaca cacaagatca cacagcatgg agtctcgacc     27300
```

```
caatggtagt gcccaagatc acttggctcg ggctcctacc tatagtccca atttgggaat   27360
gacataaagt caagtacaca agatcactta gcctggtacc aacattccat gtcggcaaac   27420
acgtttttcc agcgatgagc ccttgtgtct caaacgcctt cttcgggcat ccacctttct   27480
catgtaaatc aatgcattca aatttcatct tattcaatga catgtcgtat tctgtagggt   27540
atcatcatac ccgactttct agtcatcaat atcacatcca catatgcata atcacgtaaa   27600
aaccaaggtg cttcatcatt tacaagtggt gaacaatatt tatttcaaat tcatgctctc   27660
ttttgttgat cacaatacaa tatggagcat cgaaacatta tcatgagaat ttgaaaacaa   27720
tttatcattt atatttatca aacttccatg aaaatctca aatcacatat gcatagtttc      27780
aaccattgaa gtatataggc aaacaattcc catgacataa agaaaacgac ttagaaatcg   27840
tattgaaagc aagatattag catttgattg aaaaccccca tttaaaagca tgcatgttca   27900
taaaaactac acccatgaga ttttttggata accccactac ctctatttcc aaggataata   27960
gatgtttctt gaagcttgcg gattgttgat tccaaatatg taattatctt tgaaaaccta   28020
cggtcaaatc ttgaactatt tgggttttta ttttgaaacc ctaaggagaa tcttgagcac   28080
ttttgatgaa agaatatgta ttttggggtc cttggaacta atctcgtgt tttagggcta      28140 agtaagggtg gaaaagaacc actttgtcct caacacggag tgtttaaatc accagaattc   28200
gttacatagg caccgcctat gctatcgcct atgtttacat aggcgccgcc tacgctattg    28260
cctatgcttt tcagtggcca tggggcattg gttaggcgac gcttatcact ttgaagggcc   28320
ataacttctt gctcgggtgt cggattttag ccaaattggt atcgttggaa agctaccttg    28380
aatacctatc atttgacaca tagtaggctt cctaattcga catatacaga gagttatggt   28440
cgatggaagc tgcacacactt tacaacgtcc actaaaactt gatcgaaata gtttcaattc   28500
gtccttgagt tgaaggacct ctatggtcta atttcaagct tgagtggatt cacatgctac   28560
gcaataatta acatgccgta ttggcatgat tttatggctt cgggataagc aacgcatcga   28620
aatcatggtc tatattgtag ccgaattgcg gggcgttaca gcaaggctcc taaccattgt   28680
cccaatttgg gatgtcataa tgtcaggtac acaaaatcac acagcagggt accaagttct   28740
cgagtcggca aacacggttt ccagcgtaga gtcatttgac tcgtgctttc tttgggtaac   28800
cacctatctc acaaaatcaa tgcattaaac tcatttaat caatcacatg tcatactctg      28860
cagggtatca tcatacccga cttgcaagtc atcaatatca catcaacttt caaacttctc   28920
ataccatgta ctacatgcac atatgtatga ctttcacccc attaaaacac atacaccatg   28980
gttctcaaca tgcaattatt taagaaattt aatcatttat gagtaatgtc atatcaattg   29040
caaaactcat gatctcaatg gttttaacac tagtataata tggggtacaa acattatcat   29100
ggggaattta gaaaattcac aactcatgta catcgcaccc ttttgaaatt tcaggtcaca   29160
tgttcacaat tcaaccattt aaatacattc aaacaaacaa ccccatgata tctcagtagt   29220
tctttcaatg tcatatatca aaacatgtta tttgtatcaa ttgaaaaccc ccatttgtaa   29280
aaacatatat gtacttgtat aaatttaaag tcttgcgtaa gttcctttt gaaaacatgc      29340 ccatgaactt taggataacc ccacgtacct ctatttacga aattagcggg tgtttcttga   29400
agcctatgac ctgggggattt tgaatcttca atcgattttg aaaatccacg gttaaatctt    29460
gggtttcttg aagttcttgt ttgaaatcct agagaggatt tttgatgatt ttaatgaaaa   29520
tagggttaag ttgctcaaac ataccctaaa tcctttgttt ggacggtttt aaaggctagg   29580
gaaaagtcaa atttacccctt aatgactcct gaatggaact ggaaatttga acttaaaaac   29640 ccgatttgg gtaccaccgc gacgtgccac aatcgcggtg gtccactgga attcaacgag    29700
```

-continued

```
tgggaaattg ggtgcctccg cgacgcgcca ccatcgcgga gcccactgaa atttgacgat    29760
tgtcaatttg accctctctg cgacatgcta gaccccaaaa tgacaatgtt tacgactgga    29820
actttaaatt attcataact tcttcaccga gggtccattt tggacgaatc ttatattgtt    29880
ggaaagctaa ttcagtcatc tacgtaatga aaggttgaaa tttagaaaat tccacatgaa    29940
aaataattta gatcattcta gaagctaatg cttagacttt ccatggacgg aacttagcta    30000
agaagacatc ggggtgttac actaatggtc atctttcacc acaatttata cccactaaca    30060
ccaaagaata atgtggtgag ttacaagact taatgtggta gataatggac aaataaagtg    30120
taaaagatta caagactttg tccacttttt attcccataa attatcatgc aaattaatat    30180
tttaatatta aaatgcataa taccccaat acaaaataaa aatgaagagt aggcgtttgc     30240
tctctttgta ggcattggac acgaatttta agttgtggat tgtataaatt ctagtaaaat    30300
aaggtttatt tcaaataatc cttttataaa acaattgaaa tatcaagaaa tgaaacttgg    30360
tataaacttt tcaatattgt tagcaagcca gcattttcaa ctttcaataa atcttttagc    30420
tgtgtccccg actccttcaa aatatctccc atccaaaaaa ttttaaattt atttatttca    30480
ttataagtaa ctttgttttg ttttgttgtt ttcttctaat gaattttatt tgcaaagata    30540
ttgtagttta ggtcacatat ccaatgtgtt cataattata ttcatcgaca tatatttatt    30600
tacttaaatg aactaatagg atgaacaaaa tatttattca tattcaatgc ttgtctcatg    30660
caaaatgatt tattataatg ttatagaaag ccaaaatttg aataagaacc tcaagatgta    30720
ggaagcattt agcttacata ttttttcaatt tggtatagtt ttggatgaat acataaatta    30780
tcttgttagg atcaaatatc gtgtctcacg cgatgagggc aaagatgtgg caggacacgt    30840
taaccaggtg acgagtgcaa tattatatat cagatcgcat aaactttctg aaactgaatg    30900
gtcaaagagg aagaactcaa gtcgattaca tctcatatat ccccgtatga tttgctcaag    30960
atgttgcttt attggacgat ccataattta gagtcagcgg attcagaata tttgtcacac    31020
ttttaaatga ttgtcatatg tgtgttcttg tgtctgtcag tgtgtgtgtg ttttctcaca    31080
tgaagttgag ttgaaagatg tgagtttggt tgagcacgca ctaaatctgc atctgaataa    31140
tgtgacttgt cgaacttcca ctgacgcttc ttgtttcttc tcagtgaagg agagtgattc    31200
tgattcagaa gaacattagg aaaggatctc aaggccagaa ggattgaact cttgggattt    31260
catttcggcc ctctatcaca aaataccact aaattatcgg tttcaagcaa tgtgtgactt    31320
ccaaggagat gtgatatctt ttgtgttgta acatattttt gagttgtact gattcccttc    31380
ttcccttctc tttttatgta actttactaa ttcaacttca agtactagca gaccacatgg    31440
ttgattgtga tcgagtttga tgattatttt atacgatgag acaaccagtt t             31491
```

<210> SEQ ID NO 2
<211> LENGTH: 3099
<212> TYPE: DNA
<213> ORGANISM: Capsicum annuum
<220> FEATURE:
<221> NAME/KEY: CDS
<222> LOCATION: (93)..(2810)
<223> OTHER INFORMATION:

<400> SEQUENCE: 2

```
caaatatttc ttggagtgaa tttgaagttg tattatctgc aattgaatgg ttggtcatag     60
tcgcaaagga caaaacgag aatacagtat at atg gct cat gca agt gtg gct        113
                                 Met Ala His Ala Ser Val Ala
                                  1               5
```

-continued

```
tct ctt atg aga aca ata gaa tct ctc ttg aca ttc aat tcg ccg atg      161
Ser Leu Met Arg Thr Ile Glu Ser Leu Leu Thr Phe Asn Ser Pro Met
         10                  15                  20 caa tct cta tcc tgt gat cac aga gaa gaa ctt tgc gct ctt cgt gaa      209
Gln Ser Leu Ser Cys Asp His Arg Glu Glu Leu Cys Ala Leu Arg Glu
 25                  30                  35 aaa gtt agt tcc ctg gaa gta ttt gtc aag aac ttt gag aaa aac aat      257
Lys Val Ser Ser Leu Glu Val Phe Val Lys Asn Phe Glu Lys Asn Asn
 40                  45                  50                  55 gtt ttt ggg gaa atg acg gat ttt gaa gta gag gta aga gaa gtt gca      305
Val Phe Gly Glu Met Thr Asp Phe Glu Val Glu Val Arg Glu Val Ala
                     60                  65                  70 agt gct gct gaa tac aca att caa ctg aga cta aca gga act gta ctg      353
Ser Ala Ala Glu Tyr Thr Ile Gln Leu Arg Leu Thr Gly Thr Val Leu
             75                  80                  85 gga gaa aat aaa agc cag aaa aaa aag gcg cgt cga agg ttt cgt caa      401
Gly Glu Asn Lys Ser Gln Lys Lys Lys Ala Arg Arg Arg Phe Arg Gln
         90                  95                 100 agc ctg caa caa gta gca gag gac atg gat cat atc tgg aaa gag tcg      449
Ser Leu Gln Gln Val Ala Glu Asp Met Asp His Ile Trp Lys Glu Ser
    105                 110                 115 aca aag atc caa gat aaa gga aaa caa gta tca aag gaa tca ttg gtt      497
Thr Lys Ile Gln Asp Lys Gly Lys Gln Val Ser Lys Glu Ser Leu Val
120                 125                 130                 135 cat gat ttt tca agt tca aca aac gat att ttg aag gtt aag aac aat      545
His Asp Phe Ser Ser Ser Thr Asn Asp Ile Leu Lys Val Lys Asn Asn
                    140                 145                 150 atg gtt gga cgt gat gat caa agg aaa cag ttg tta gaa gat ctg act      593
Met Val Gly Arg Asp Asp Gln Arg Lys Gln Leu Leu Glu Asp Leu Thr
                155                 160                 165 aga agc tac tct ggg gaa ccc aaa gtc atc ccg att gtc ggg atg gga      641
Arg Ser Tyr Ser Gly Glu Pro Lys Val Ile Pro Ile Val Gly Met Gly
            170                 175                 180 ggc ata ggt aaa aca acc tta gca aaa gaa gtt tac aat gat gaa tca      689
Gly Ile Gly Lys Thr Thr Leu Ala Lys Glu Val Tyr Asn Asp Glu Ser
        185                 190                 195 att cta tgc cgt ttt gat gtt cat gcc tgg gct acc ata tct caa cag      737
Ile Leu Cys Arg Phe Asp Val His Ala Trp Ala Thr Ile Ser Gln Gln
200                 205                 210                 215 cac aac aaa aag gaa att ttg ctg ggc ctt ctg cat tcc aca atc aaa      785
His Asn Lys Lys Glu Ile Leu Leu Gly Leu Leu His Ser Thr Ile Lys
                    220                 225                 230 atg gat gac agg gtt aag atg att ggt gaa gca gag cta gca gac atg      833
Met Asp Asp Arg Val Lys Met Ile Gly Glu Ala Glu Leu Ala Asp Met
                235                 240                 245 tta cag aaa agt tta aag aga aag agg tac tta att gtc ttg gat gat      881
Leu Gln Lys Ser Leu Lys Arg Lys Arg Tyr Leu Ile Val Leu Asp Asp
            250                 255                 260 atc tgg agt tgt gaa gtg tgg gat ggc gtg aga cga tgc ttt cca act      929
Ile Trp Ser Cys Glu Val Trp Asp Gly Val Arg Arg Cys Phe Pro Thr
        265                 270                 275 gaa gac aat gca ggg agt cga ata ctg ttg act acc cgt aat gat gaa      977
Glu Asp Asn Ala Gly Ser Arg Ile Leu Leu Thr Thr Arg Asn Asp Glu
280                 285                 290                 295 gta gct tgt tat gct ggt gta gag aat ttt tct ttg cgg atg agc ttc     1025
Val Ala Cys Tyr Ala Gly Val Glu Asn Phe Ser Leu Arg Met Ser Phe
                    300                 305                 310 atg gat caa gat gag agt tgg agt ctt ttc aaa agt gca gca ttt tca     1073
Met Asp Gln Asp Glu Ser Trp Ser Leu Phe Lys Ser Ala Ala Phe Ser
                315                 320                 325
```

-continued

| | |
|---|---|
| agt gaa gca tta cca tat gag ttc gag act gtt gga aag caa atc gca<br>Ser Glu Ala Leu Pro Tyr Glu Phe Glu Thr Val Gly Lys Gln Ile Ala<br>330                    335                    340 | 1121 |
| gat gaa tgt cac ggg tta cca cta act att gtc gtg gtt gca ggg ctt<br>Asp Glu Cys His Gly Leu Pro Leu Thr Ile Val Val Val Ala Gly Leu<br>345                    350                    355 | 1169 |
| ctc aaa tct aaa agg aca ata gaa gat tgg aaa act gtt gct aaa gat<br>Leu Lys Ser Lys Arg Thr Ile Glu Asp Trp Lys Thr Val Ala Lys Asp<br>360                    365                    370                    375 | 1217 |
| gtc aag tca ttc gtc aca aat gat cct gat gaa cga tgt tca cgt gtg<br>Val Lys Ser Phe Val Thr Asn Asp Pro Asp Glu Arg Cys Ser Arg Val<br>                    380                    385                    390 | 1265 |
| ctt ggg ttg agt tac gat cac ttg aca agc gat cta aaa aca tgt ctt<br>Leu Gly Leu Ser Tyr Asp His Leu Thr Ser Asp Leu Lys Thr Cys Leu<br>                    395                    400                    405 | 1313 |
| ctg cat ttc gga att ttt cca gaa gac agt gat att cca gtg aag aat<br>Leu His Phe Gly Ile Phe Pro Glu Asp Ser Asp Ile Pro Val Lys Asn<br>410                    415                    420 | 1361 |
| ttg atg aga tca tgg atg gct gag ggg ttc ctg aag ttg gaa aat gat<br>Leu Met Arg Ser Trp Met Ala Glu Gly Phe Leu Lys Leu Glu Asn Asp<br>425                    430                    435 | 1409 |
| ttg gaa gga gag gtt gag aag tgt ttg caa gag ctt gtc gat aga tgt<br>Leu Glu Gly Glu Val Glu Lys Cys Leu Gln Glu Leu Val Asp Arg Cys<br>440                    445                    450                    455 | 1457 |
| cta gtc ctc gtc agc aag aga agt cga gat gga aca aaa att aga tca<br>Leu Val Leu Val Ser Lys Arg Ser Arg Asp Gly Thr Lys Ile Arg Ser<br>                    460                    465                    470 | 1505 |
| tgt aag gtt cat gat cta ata tat gac ctg tgc gtg aga gaa gtt caa<br>Cys Lys Val His Asp Leu Ile Tyr Asp Leu Cys Val Arg Glu Val Gln<br>                    475                    480                    485 | 1553 |
| agg gag aac att ttt atc atg aac gac att gtt ctt gac gta tca tat<br>Arg Glu Asn Ile Phe Ile Met Asn Asp Ile Val Leu Asp Val Ser Tyr<br>490                    495                    500 | 1601 |
| cca gaa tgt tca tat ctc tgt atg tat aaa atg cag ccc ttt aag cgc<br>Pro Glu Cys Ser Tyr Leu Cys Met Tyr Lys Met Gln Pro Phe Lys Arg<br>505                    510                    515 | 1649 |
| gtg act ggt gat gaa att aat tat tgt ccc tat ggt ctt tat agg gct<br>Val Thr Gly Asp Glu Ile Asn Tyr Cys Pro Tyr Gly Leu Tyr Arg Ala<br>520                    525                    530                    535 | 1697 |
| ctt ctt acc cct gta aat cgt cag ttg aga gat cat gac aac aac aat<br>Leu Leu Thr Pro Val Asn Arg Gln Leu Arg Asp His Asp Asn Asn Asn<br>                    540                    545                    550 | 1745 |
| ctt ttg aaa cga acc cat tct gtt ttc tct ttt cat ctt gag cct tta<br>Leu Leu Lys Arg Thr His Ser Val Phe Ser Phe His Leu Glu Pro Leu<br>                    555                    560                    565 | 1793 |
| tat tat gtt ctc aaa tca gag gtt gtt cat ttc aaa tta ctc aaa gtc<br>Tyr Tyr Val Leu Lys Ser Glu Val Val His Phe Lys Leu Leu Lys Val<br>570                    575                    580 | 1841 |
| ttg gag ctg aga cac aga cag att gat ggt ttc cct cga gag ata cta<br>Leu Glu Leu Arg His Arg Gln Ile Asp Gly Phe Pro Arg Glu Ile Leu<br>585                    590                    595 | 1889 |
| agc ctc atc tgg ttg agg tac cta tca ttg ttc agc tat ggg aat ttc<br>Ser Leu Ile Trp Leu Arg Tyr Leu Ser Leu Phe Ser Tyr Gly Asn Phe<br>600                    605                    610                    615 | 1937 |
| gat gta cct cca gaa att tgc agg tta tgg aat ctg cag aca ttc att<br>Asp Val Pro Pro Glu Ile Cys Arg Leu Trp Asn Leu Gln Thr Phe Ile<br>                    620                    625                    630 | 1985 |
| gtt caa cgg ttt cga tca gat ata ata att ttt gct gag gaa att tgg<br>Val Gln Arg Phe Arg Ser Asp Ile Ile Ile Phe Ala Glu Glu Ile Trp | 2033 |

-continued

```
                 635                 640                 645
gaa cta atg caa tta agg cat ctt aaa ctg ccc aga ttt tat ttg cca        2081
Glu Leu Met Gln Leu Arg His Leu Lys Leu Pro Arg Phe Tyr Leu Pro
        650                 655                 660 gat tgc cca agt gga tct gtt gac aaa gga agg cac ttg gat ttt tca        2129
Asp Cys Pro Ser Gly Ser Val Asp Lys Gly Arg His Leu Asp Phe Ser
665                 670                 675 aac tta caa act att tct tac ttg tct cca cgt tgt tgc acg aag gag        2177
Asn Leu Gln Thr Ile Ser Tyr Leu Ser Pro Arg Cys Cys Thr Lys Glu
680                 685                 690                 695 gtt att atg ggg att cag aat gtc aaa aaa tta gga atc agt gga aat        2225
Val Ile Met Gly Ile Gln Asn Val Lys Lys Leu Gly Ile Ser Gly Asn
                700                 705                 710 aag gat gac tat aaa agt ttt cgg gac tct ggg ctt ccc aac aat ctt        2273
Lys Asp Asp Tyr Lys Ser Phe Arg Asp Ser Gly Leu Pro Asn Asn Leu
            715                 720                 725 gtc tat ctg cag caa ctt gaa ata ttg agt ctt ata tct gtt gat tat        2321
Val Tyr Leu Gln Gln Leu Glu Ile Leu Ser Leu Ile Ser Val Asp Tyr
        730                 735                 740 agc ctt ttg cca gtg atc att tca agt gca aaa gct ttt cca gca acg        2369
Ser Leu Leu Pro Val Ile Ile Ser Ser Ala Lys Ala Phe Pro Ala Thr
    745                 750                 755 ctc aag aag ttg aag ttg gaa aga act tat cta agc tgg tca tac ttg        2417
Leu Lys Lys Leu Lys Leu Glu Arg Thr Tyr Leu Ser Trp Ser Tyr Leu
760                 765                 770                 775 gac atc ata gct gag ttg cct aac ctt gag gtg ctg aag ctg atg gat        2465
Asp Ile Ile Ala Glu Leu Pro Asn Leu Glu Val Leu Lys Leu Met Asp
                780                 785                 790 gac gct tgt tgt ggt gaa gaa tgg cat cca att gtt atg gga ttt aat        2513
Asp Ala Cys Cys Gly Glu Glu Trp His Pro Ile Val Met Gly Phe Asn
            795                 800                 805 cga ttg aag ctt ttg cta att aaa tat agt ttt ctc aag ttc tgg aaa        2561
Arg Leu Lys Leu Leu Leu Ile Lys Tyr Ser Phe Leu Lys Phe Trp Lys
        810                 815                 820 gcc aca aat gac aat ttt cct gtc ctt gag cgc ctc atg att aga agt        2609
Ala Thr Asn Asp Asn Phe Pro Val Leu Glu Arg Leu Met Ile Arg Ser
    825                 830                 835 tgc aaa aat ttg aaa gag ata ccc att gag ttt gca gat ata cac aca        2657
Cys Lys Asn Leu Lys Glu Ile Pro Ile Glu Phe Ala Asp Ile His Thr
840                 845                 850                 855 cta cag ctg att gag tta aga gag tgt cct ccc aaa ctt ggg gaa tct        2705
Leu Gln Leu Ile Glu Leu Arg Glu Cys Pro Pro Lys Leu Gly Glu Ser
                860                 865                 870 gct gca cga att cag aaa gaa caa gaa gac ctc gga aac aac cct gtg        2753
Ala Ala Arg Ile Gln Lys Glu Gln Glu Asp Leu Gly Asn Asn Pro Val
            875                 880                 885 gat gtt cgt atc tca aat cca ttg aag gag agt gat tct gat tca gaa        2801
Asp Val Arg Ile Ser Asn Pro Leu Lys Glu Ser Asp Ser Asp Ser Glu
        890                 895                 900 gaa cat tag gaaaggatct caaggccaga aggattgaac tcttgggatt              2850
Glu His
    905 tcatttcggc cctctatcac aaaataccac taaattatcg gtttcaagca atgtgtgact      2910 tccaaggaga tgtgatatct tttgtgttgt aacatatttt tgagttgtac tgattccctt      2970 cttcccttct cttttatgt aactttacta attcaacttc aagtactagc agaccacatg       3030 gttgattgtg atcgagtttg atgattattt tatacgatga gacaaccagt ttagttttaa      3090 aaaaaaaaa                                                              3099
```

<210> SEQ ID NO 3
<211> LENGTH: 905
<212> TYPE: PRT
<213> ORGANISM: Capsicum annuum

<400> SEQUENCE: 3

```
Met Ala His Ala Ser Val Ala Ser Leu Met Arg Thr Ile Glu Ser Leu
1               5                   10                  15

Leu Thr Phe Asn Ser Pro Met Gln Ser Leu Ser Cys Asp His Arg Glu
            20                  25                  30

Glu Leu Cys Ala Leu Arg Glu Lys Val Ser Ser Leu Glu Val Phe Val
        35                  40                  45

Lys Asn Phe Glu Lys Asn Asn Val Phe Gly Glu Met Thr Asp Phe Glu
    50                  55                  60

Val Glu Val Arg Glu Val Ala Ser Ala Ala Glu Tyr Thr Ile Gln Leu
65                  70                  75                  80

Arg Leu Thr Gly Thr Val Leu Gly Glu Asn Lys Ser Gln Lys Lys Lys
                85                  90                  95

Ala Arg Arg Arg Phe Arg Gln Ser Leu Gln Gln Val Ala Glu Asp Met
            100                 105                 110

Asp His Ile Trp Lys Glu Ser Thr Lys Ile Gln Asp Lys Gly Lys Gln
        115                 120                 125

Val Ser Lys Glu Ser Leu Val His Asp Phe Ser Ser Thr Asn Asp
    130                 135                 140

Ile Leu Lys Val Lys Asn Asn Met Val Gly Arg Asp Asp Gln Arg Lys
145                 150                 155                 160

Gln Leu Leu Glu Asp Leu Thr Arg Ser Tyr Ser Gly Glu Pro Lys Val
                165                 170                 175

Ile Pro Ile Val Gly Met Gly Gly Ile Gly Lys Thr Thr Leu Ala Lys
            180                 185                 190

Glu Val Tyr Asn Asp Glu Ser Ile Leu Cys Arg Phe Asp Val His Ala
        195                 200                 205

Trp Ala Thr Ile Ser Gln Gln His Asn Lys Lys Glu Ile Leu Leu Gly
    210                 215                 220

Leu Leu His Ser Thr Ile Lys Met Asp Asp Arg Val Lys Met Ile Gly
225                 230                 235                 240

Glu Ala Glu Leu Ala Asp Met Leu Gln Lys Ser Leu Lys Arg Lys Arg
                245                 250                 255

Tyr Leu Ile Val Leu Asp Asp Ile Trp Ser Cys Glu Val Trp Asp Gly
            260                 265                 270

Val Arg Arg Cys Phe Pro Thr Glu Asp Asn Ala Gly Ser Arg Ile Leu
        275                 280                 285

Leu Thr Thr Arg Asn Asp Glu Val Ala Cys Tyr Ala Gly Val Glu Asn
    290                 295                 300

Phe Ser Leu Arg Met Ser Phe Met Asp Gln Asp Glu Ser Trp Ser Leu
305                 310                 315                 320

Phe Lys Ser Ala Ala Phe Ser Ser Glu Ala Leu Pro Tyr Glu Phe Glu
                325                 330                 335

Thr Val Gly Lys Gln Ile Ala Asp Glu Cys His Gly Leu Pro Leu Thr
            340                 345                 350

Ile Val Val Val Ala Gly Leu Leu Lys Ser Lys Arg Thr Ile Glu Asp
        355                 360                 365

Trp Lys Thr Val Ala Lys Asp Val Lys Ser Phe Val Thr Asn Asp Pro
```

-continued

```
                370                 375                 380
Asp Glu Arg Cys Ser Arg Val Leu Gly Leu Ser Tyr Asp His Leu Thr
385                 390                 395                 400

Ser Asp Leu Lys Thr Cys Leu Leu His Phe Gly Ile Phe Pro Glu Asp
                405                 410                 415

Ser Asp Ile Pro Val Lys Asn Leu Met Arg Ser Trp Met Ala Glu Gly
                420                 425                 430

Phe Leu Lys Leu Glu Asn Asp Leu Glu Gly Glu Val Glu Lys Cys Leu
                435                 440                 445

Gln Glu Leu Val Asp Arg Cys Leu Val Leu Val Ser Lys Arg Ser Arg
450                 455                 460

Asp Gly Thr Lys Ile Arg Ser Cys Lys Val His Asp Leu Ile Tyr Asp
465                 470                 475                 480

Leu Cys Val Arg Glu Val Gln Arg Glu Asn Ile Phe Ile Met Asn Asp
                485                 490                 495

Ile Val Leu Asp Val Ser Tyr Pro Glu Cys Ser Tyr Leu Cys Met Tyr
                500                 505                 510

Lys Met Gln Pro Phe Lys Arg Val Thr Gly Asp Glu Ile Asn Tyr Cys
                515                 520                 525

Pro Tyr Gly Leu Tyr Arg Ala Leu Leu Thr Pro Val Asn Arg Gln Leu
                530                 535                 540

Arg Asp His Asp Asn Asn Asn Leu Leu Lys Arg Thr His Ser Val Phe
545                 550                 555                 560

Ser Phe His Leu Glu Pro Leu Tyr Tyr Val Leu Lys Ser Glu Val Val
                565                 570                 575

His Phe Lys Leu Leu Lys Val Leu Glu Leu Arg His Arg Gln Ile Asp
                580                 585                 590

Gly Phe Pro Arg Glu Ile Leu Ser Leu Ile Trp Leu Arg Tyr Leu Ser
                595                 600                 605

Leu Phe Ser Tyr Gly Asn Phe Asp Val Pro Pro Glu Ile Cys Arg Leu
                610                 615                 620

Trp Asn Leu Gln Thr Phe Ile Val Gln Arg Phe Arg Ser Asp Ile Ile
625                 630                 635                 640

Ile Phe Ala Glu Glu Ile Trp Glu Leu Met Gln Leu Arg His Leu Lys
                645                 650                 655

Leu Pro Arg Phe Tyr Leu Pro Asp Cys Pro Ser Gly Ser Val Asp Lys
                660                 665                 670

Gly Arg His Leu Asp Phe Ser Asn Leu Gln Thr Ile Ser Tyr Leu Ser
                675                 680                 685

Pro Arg Cys Cys Thr Lys Glu Val Ile Met Gly Ile Gln Asn Val Lys
                690                 695                 700

Lys Leu Gly Ile Ser Gly Asn Lys Asp Asp Tyr Lys Ser Phe Arg Asp
705                 710                 715                 720

Ser Gly Leu Pro Asn Asn Leu Val Tyr Leu Gln Gln Leu Glu Ile Leu
                725                 730                 735

Ser Leu Ile Ser Val Asp Tyr Ser Leu Leu Pro Val Ile Ile Ser Ser
                740                 745                 750

Ala Lys Ala Phe Pro Ala Thr Leu Lys Leu Lys Leu Glu Arg Thr
                755                 760                 765

Tyr Leu Ser Trp Ser Tyr Leu Asp Ile Ile Ala Glu Leu Pro Asn Leu
                770                 775                 780

Glu Val Leu Lys Leu Met Asp Asp Ala Cys Cys Gly Glu Glu Trp His
785                 790                 795                 800
```

```
Pro Ile Val Met Gly Phe Asn Arg Leu Lys Leu Leu Ile Lys Tyr
            805                 810                 815

Ser Phe Leu Lys Phe Trp Lys Ala Thr Asn Asp Asn Phe Pro Val Leu
                820                 825                 830

Glu Arg Leu Met Ile Arg Ser Cys Lys Asn Leu Lys Glu Ile Pro Ile
            835                 840                 845

Glu Phe Ala Asp Ile His Thr Leu Gln Leu Ile Glu Leu Arg Glu Cys
        850                 855                 860

Pro Pro Lys Leu Gly Glu Ser Ala Ala Arg Ile Gln Lys Glu Gln Glu
865                 870                 875                 880

Asp Leu Gly Asn Asn Pro Val Asp Val Arg Ile Ser Asn Pro Leu Lys
                885                 890                 895

Glu Ser Asp Ser Asp Ser Glu Glu His
            900                 905

<210> SEQ ID NO 4
<211> LENGTH: 2718
<212> TYPE: DNA
<213> ORGANISM: Capsicum annuum

<400> SEQUENCE: 4
```

| | |
|---|---|
| atggctcatg caagtgtggc ttctcttatg agaacaatag aatctctctt gacattcaat | 60 |
| tcgccgatgc aatctctatc ctgtgatcac agagaagaac tttgcgctct tcgtgaaaaa | 120 |
| gttagttccc tggaagtatt tgtcaagaac tttgagaaaa acaatgtttt tggggaaatg | 180 |
| acggattttg aagtagaggt aagagaagtt gcaagtgctg ctgaatacac aattcaactg | 240 |
| agactaacag gaactgtact gggagaaaat aaaagccaga aaaaaaaggc gcgtcgaagg | 300 |
| tttcgtcaaa gcctgcaaca gtagcagag gacatggatc atatctggaa agagtcgaca | 360 |
| aagatccaag ataaaggaaa acaagtatca aggaatcat tggttcatga tttttcaagt | 420 |
| tcaacaaacg atattttgaa ggttaagaac aatatggttg acgtgatga tcaaaggaaa | 480 |
| cagttgttag aagatctgac tagaagctac tctggggaac ccaaagtcat cccgattgtc | 540 |
| gggatgggag gcataggtaa acaaccttta gcaaaagaag tttacaatga tgaatcaatt | 600 |
| ctatgccgtt ttgatgttca tgcctgggct accatatctc aacagcacaa caaaaaggaa | 660 |
| attttgctgg gccttctgca ttccacaatc aaaatggatg acagggttaa gatgattggt | 720 |
| gaagcagagc tagcagacat gttacagaaa gtttaaaga aaagaggta cttaattgtc | 780 |
| ttggatgata tctggagttg tgaagtgtgg atggcgtga cgatgctt tccaactgaa | 840 |
| gacaatgcag ggagtcgaat actgttgact acccgtaatg atgaagtagc ttgttatgct | 900 |
| ggtgtagaga atttttcttt gcggatgagc ttcatggatc aagatgagag ttggagtctt | 960 |
| ttcaaaagtg cagcatttc aagtgaagca ttaccatatg agttcgagac tgttggaaag | 1020 |
| caaatcgcag atgaatgtca cgggttacca ctaactattg tcgtggttgc agggcttctc | 1080 |
| aaatctaaaa ggacaataga agattggaaa actgttgcta agatgtcaa gtcattcgtc | 1140 |
| acaaatgatc ctgatgaacg atgttcacgt gtgcttggt tgagttacga tcacttgaca | 1200 |
| agcgatctaa aaacatgtct tctgcatttc ggaattttc agaagacag tgatattcca | 1260 |
| gtgaagaatt tgatgagatc atggatggct gaggggttcc tgaagttgga aaatgatttg | 1320 |
| gaaggagagg ttgagaagtg tttgcaagag cttgtcgata gatgtctagt cctcgtcagc | 1380 |
| aagagaagtc gagatggaac aaaaattaga tcatgtaagg ttcatgatct aatatatgac | 1440 |
| ctgtgcgtga gagaagttca aagggagaac attttttatca tgaacgacat tgttcttgac | 1500 |

```
gtatcatatc cagaatgttc atatctctgt atgtataaaa tgcagccctt taagcgcgtg    1560
actggtgatg aaattaatta ttgtccctat ggtctttata gggctcttct taccgctgta    1620
aatcgtcagt tgagagatca tgacaacaac aatcttttga aacgaaccca ttctgttttc    1680
tcttttcatc ttgagccttt atattatgtt ctcaaatcag aggttgttca tttcaaatta    1740
ctcaaagtct tggagctgag acacagacag attgatggtt ccctcgaga  gatactaagc    1800 ctcatctggt tgaggtacct atcattgttc agctatggga atttcgatgt acctccagaa    1860
atttgcaggt tatggaatct gcagacattc attgttcaac ggtttcgatc agatataata    1920
atttttgctg aggaaatttg ggaactaatg caattaaggc atcttaaact gcccagattt    1980
tatttgccag attgcccaag tggatctgtt gacaaaggaa ggcacttgga tttttcaaac    2040
ttacaaacta tttcttactt gtctccacgt tgttgcacga aggaggttat tatggggatt    2100
cagaatgtca aaaaattagg aatcagtgga aataaggatg actataaaag ttttcgggac    2160
tctgggcttc ccaacaatct tgtctatctg cagcaacttg aaatattgag tcttatatct    2220
gttgattata gccttttgcc agtgatcatt tcaagtgcaa aagcttttcc agcaacgctc    2280
aagaagttga agttggaaag aacttatcta agctggtcat acttggacat catagctgag    2340
ttgcctaacc ttgaggtgct gaagctgatg gatgacgctt gttgtggtga agaatggcat    2400
ccaattgtta tgggatttaa tcgattgaag cttttgctaa ttaaatatag ttttctcaag    2460
ttctggaaag ccacaaatga caatttttcct gtccttgagc gcctcatgat tagaagttgc    2520
aaaaatttga aagagatacc cattgagttt gcagatatac acacactaca gctgattgag    2580
ttaagagagt gtcctcccaa acttggggaa tctgctgcac gaattcagaa agaacaagaa    2640
gacctcggaa acaaccctgt ggatgttcgt atctcaaatc cattgaagga gagtgattct    2700
gattcagaag aacattag                                                  2718

<210> SEQ ID NO 5
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 5
caaatatttc ttggagtgaa tttga                                            25

<210> SEQ ID NO 6
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 6
aaaactaaac tggttgtctc atcgt                                            25

<210> SEQ ID NO 7
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 7
atggctcatg caagtgtggc ttctc                                            25
```

```
<210> SEQ ID NO 8
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 8
ctaatgttct tctgaatcag aatca                                        25

<210> SEQ ID NO 9
<211> LENGTH: 2053
<212> TYPE: DNA
<213> ORGANISM: Capsicum annuum

<400> SEQUENCE: 9
cgtgggtggg gggttggaca caacccaaa taccatgaat ttggttttct agtttttatat    60 agacaaatat atgtacatga gttagtacaa tttcgtagaa aaaatcaaca ttctgttgac   120
caagaaaatt attagtattt tttttttaaa aaagtagttt gggaaagtta gtatatgtaa   180
cattcttatt ttcttgtcag ttagtaatgg atcaagcttt ttagtatttt tatgacgata   240
ttacaataac aacaacaaca tatttagtga attttcatag gtgagatatc tgatctaaga   300
cgatattgca tacataaaaa atcttatgga atattggaat agtataataa ggtcacaagt   360
ggaacaataa ttatttactt agattagaat attattgggg taatgacttt tggtataata   420
agtcaatgaa tgatgtgaaa tttggtgaac atgtttagat aatttaaata caatttgaca   480
agtgatgata caaattgacc aagtcatcta agcttataaa tttgataaca ctttattaat   540
tcttgattct tctaaaagtc aatcaatgg gtttcatgtt tggttttcat tgtttctctt   600
ttttcctttg actctaaata gaaggtgtgg aggttactaa aaaggagtgt gtcttattct   660
ggtagatagg agtgctttgt tttggtatcc gtgctagtag tcatagcgtt aagcttgtac   720
tgtcttgttt gtggagtttt gataataatt attgtttcag ataggtctat tggaatacta   780
cttttttttg ttaactattt tttgtcttgt tatttgtgca agtagtcata gtactatacc   840
tgtactatta tttgttctgt tattagatgt ccgtaaagat tgtgtcctct catgagcatg   900
gatacttgtt ctttccatag agaaaaatta tgattgccag caagtttaat cagaagttgg   960
gtaaccgagt tgaattgaac aagattggtg aagttggttg catcggagtt gctaacagag  1020
agagagagag agagagccat ttctgatggt tgggtaaaaa aaatcttaga actccgtgag  1080
aagaaaaaaa gctcttgata ccatgtaaag gtttgagatg tagaagagaa agataaatgt  1140
tattcacgta caacagctct ttatagagcg gatacaaact atgtgataag tacaaagaag  1200
caaacacact taaaatatag gaaactatga gactcctaaa tataacacat aactaactaa  1260
cataattgcg tatatcttga tagctataat attttaagct aataacaaac tggaggtgac  1320
atatattatc gtacagcggg actcgtccaa tcagataata atgacgatga tgataatgaa  1380
gattcagatg ctgatgataa taaagattct gatgctgatg ttgatgttgc agaacatgat  1440
ggttgttatc tgttcagaat aacctgtaat gagaagggaa attatagaat aacaatttta  1500
tactgttata gactgctgat gctagttcag cacactaccg tttattcata aatgtaaatg  1560
tattaccttc tttgcagctc atttcttgaa ttagaaaatt gttgttagtt gagatgtaat  1620
ataagctttt tagctctcca gaaaatatag ttccaacatt tcgaatcgtt agaagttcga  1680
aagatgatat agtacacaat aataaaaata atagtgcgga cactgattct gaattaatc   1740 ccgaaattag ttatgtaaaa gaacgaagaa gaaaacaaat ggcagtcacg atgcgagtgg  1800
```

```
tatgataaaa atcattctgg aagaaaattg ttatctatga ggaagttgct tgattacatg      1860
aactccaaaa gtgcagcctt tttgcagaaa taaaggacca tttgtgttca gcattatata      1920
ataaggacct aagtgaatct actatttaaa gttaagggac tatttatgct gataaattct      1980
gcagatatca tttcaaaact ctttatcttt tgttcttata cacataatat tgtcatttct      2040
tctatcattt tct                                                         2053

<210> SEQ ID NO 10
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 10
cctctagatg gctcatgcaa gtgtgcgttc tcttatg                               37

<210> SEQ ID NO 11
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 11
cctctagaca aaatatttct tggagtgaat tga                                   34

<210> SEQ ID NO 12
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 12
ccatcccaca cttcacaact cca                                              23

<210> SEQ ID NO 13
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 13
gtccttgagc gcctcatg                                                    18

<210> SEQ ID NO 14
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 14
actaaactgg gtgtctcatc gt                                               22
```

BS2 RESISTANCE PROTEIN

CROSS-REFERENCE TO RELATED APPLICATIONS

This application is a divisional of U.S. application Ser. No. 09/360,186, filed Jul., 23, 1999, now U.S. Pat. No. 6,262,343 which claims priority from U.S. Provisional Application No. 60/093,957, filed Jul. 23, 1998; all of which are hereby incorporated herein in their entirety by reference.

FIELD OF THE INVENTION

This invention relates to plant disease resistance, in particular to plant genes conferring pathogen resistance.

BACKGROUND OF THE INVENTION

Plants are hosts to thousands of infectious diseases caused by a vast array of phytopathogenic fungi, bacteria, viruses, and nematodes. Plants recognize and resist many invading phytopathogens by inducing a rapid defense response, termed the hypersensitive response (HR). HR results in localized cell and tissue death at the site of infection, which constrains further spread of the infection. This local response often triggers non-specific resistance throughout the plant, a phenomenon known as systemic acquired resistance (SAR). Once triggered, SAR provides resistance for days to a wide range of pathogens. The generation of the HR and SAR in a plant depends upon the interaction between a dominant or semi-dominant resistance (R) gene product in the plant and a corresponding dominant avirulence (Avr) gene product expressed by the invading phytopathogen. It has been proposed that phylopathogen Avr products function as ligands, and that plant R products function as receptors. Thus, in the widely held model of phytopathogen/plant interaction, binding of the Avr product of an invading pathogen to a corresponding R product in the plant initiates the chain of events within the plant that produces HR and SAR and ultimately leads to disease resistance.

The production of transgenic plants carrying a heterologous gene sequence is now routinely practiced by plant molecular biologists. Methods for incorporating an isolated gene sequence into an expression cassette, producing plant transformation vectors, and transforming many types of plants are well known. Examples of the production of transgenic plants having modified characteristics as a result of the introduction of a heterologous transgene include: U.S. Pat. No. 5,719,046 to Guerineau (production of herbicide resistant plants by introduction of bacterial dihydropteroate synthase gene); U.S. Pat. No. 5,231,020 to Jorgensen (modification of flavenoids in plants); U.S. Pat. No. 5,583,021 to Dougherty (production of virus resistant plants); and U.S. Pat. No. 5,767,372 to De Greve and U.S. Pat. No. 5,500,365 to Fischoff (production of insect resistant plants by introducing *Bacillus thuringiensis* genes).

In conjunction with such techniques, the isolation of plant R genes has similarly permitted the production of plants having enhanced resistance to certain pathogens. Since the cloning of the first R gene, Pto from tomato, which confers resistance to *Pseudomonas syringae* pv. tomato (Martin et al., 1993), a number of other R genes have been reported (Hammond-Kosack and Jones, 1997). A number of these genes have been used to introduce the encoded resistance characteristic into plant lines that were previously susceptible to the corresponding pathogen. For example, U.S. Pat. No. 5,571,706 describes the introduction of the N gene into tobacco lines that are susceptible to Tobacco Mosaic Virus (TMV) in order to produce TMV-resistant tobacco plants. WO 95/28423 describes the creation of transgenic plants carrying the Rps2 gene from *Arabidopsis thaliana*, as a means of creating resistance to bacterial pathogens including *Pseudomonas syringae*, and WO 98/02545 describes the introduction of the Prf gene into plants to obtain broad-spectrum pathogen resistance.

Bacterial spot disease of tomato and pepper, caused by the phytopathogenic bacterium *Xanthomonas campestris* pv. vesicatoria (Xcv), can be devastating to commercial production of these crops in areas of the world with high humidity and heavy rainfall. While control of Xcv in commercial agriculture is based largely on the application of pesticides, genetic resistance to bacterial spot disease has been described in both tomato and pepper (Cook and Stall, 1963; Cook and Guevara, 1984; Kim and Hartmann, 1985; Jones and Scott, 1986). Of the two hosts, genetic resistance in pepper has been more well characterized. Several single loci (Bs1, Bs2, and Bs3) that confer resistance in a "gene-for-gene" manner have been identified (Hibberd et al., 1987). Moreover, the corresponding avirulence genes (avrBs1, avrBs2, and avrBs3) have been cloned from Xcv (Swanson et al., 1988; Minsavage et al., 1990). Genetic and molecular characterization of these avirulence genes has provided a great deal of information concerning the interaction between Xcv and pepper (Kearney et al., 1988; Kearney and Staskawicz, 1990; Herbers et al., 1992; Van den Ackerveken et al., 1996).

Of particular interest is the interaction governed by the avirulence gene avrBs2 and the resistance gene Bs2. AvrBs2 was originally identified as a 2.3 kb DNA fragment located on the Xcv chromosome (Minsavage et al., 1990; Kearney, 1989). Recently, it was established that avrBs2 encodes a protein with some homology to *A. tumefaciens* agrocinopine synthase and *E. coli* UgpQ, suggesting a possible enzymatic function (Swords et al., 1996). Mutant Xcv strains in which the avrBs2 gene has been disrupted or replaced are less virulent on susceptible hosts and are only able to grow to levels similar to that of wild type strains in a resistant host (Kearney, 1989; Kearney and Staskawicz, 1990; Swords et al., 1996). In addition, a survey of various races of Xcv and other pathovars of *X. campestris* has shown that avrBs2 is very widespread (Kearney and Staskawicz, 1990). For example, avrBs2 activity was shown to be present in *Xc campestris* (the causative agent of black rot in crucifers), *Xc oryzae* (now termed *X. oryzae* pv. oryzae (the causative agent of bacterial blight in rice), *Xc citri* (now termed *X. axonopodis* (the causative agent of citrus canker) and *Xc phaseoli* (the causative agent of bacterial blight of bean) (Kearney and Staskawicz, 1990). These studies also suggest that avrBs2 plays a highly conserved role in the fitness of *X. campestris*; isolates having avrBs2 show enhanced vigor on susceptible plant lines. The effectiveness of the Bs2 resistance gene against the some of the major races of Xcv appears to be based on this dual phenotype (fitness and elicitation of Bs2-mediated HR response) of the avrBs2 gene (Kearney and Staskawicz, 1990).

The availability of the Bs2 gene would facilitate the production of transgenic plants having resistance to a potentially wide range of phylopathogens. It is to such a gene that the present invention is directed.

SUMMARY OF THE INVENTION

The invention provides an isolated Bs2 gene from pepper that is shown to confer resistance to *Xanthomonas campestris* pv. vesicatoria when introduced into plants that are otherwise susceptible to infection by this organism. Specifically, such plants develop a hypersensitive response to the pathogen at the site of inoculation and show an enhanced resistance to systemic infection.

In one aspect of this invention, the nucleic acid sequences of the Bs2 gene and cDNA from pepper are provided, as is the amino acid sequence of the pepper Bs2 protein. The functional hallmark of the Bs2 protein is that it has Bs2 biological activity: when co-expressed in a plant with a *Xanthomonas campestris* AvrBs2 gene product, it produces a localized hypersensitive response, as determined by a transient assay technique described in detail below.

The existence of Bs2 homologs in other plant species including tomato and tobacco is demonstrated, and the invention provides the structural features and functional characteristics of such homologs and teaches how they may be isolated. Because the pepper Bs2 gene is the first Bs2 gene to have been isolated, it is referred to as the prototypical Bs2 gene; and the pepper Bs2 protein is referred to as the prototypical Bs2 protein. Homologs of the Bs2 protein are proteins that possess Bs2 biological activity and share a specified level of sequence identity with the prototype pepper Bs2 protein (typically at least 50% amino acid sequence identity). Nucleic acid molecules that encode such homologs are also encompassed by the invention.

In another aspect of the invention, nucleic acid molecules are provided that comprise a minimum number of consecutive nucleotides of the disclosed Bs2 sequences (e.g., at least 15 consecutive nucleotides of the pepper Bs2 cDNA). These molecules are useful, among other things, as PCR primers for amplifying portions of a Bs2 nucleic acid molecule, as sequencing primers to verify the authenticity of an amplified molecule, and as hybridization probes.

The invention also provides recombinant nucleic acid molecules that comprise a promoter sequence operably linked to a Bs2 open reading frame. Such molecules may be introduced into plants so as to confer enhanced resistance to phytopathogens such as *Xanthomonas campestris*. Transgenic plants comprising these molecules are also provided by the invention. Plants that may be usefully transformed with a Bs2 nucleic acid molecules to confer enhanced pathogen resistance include pepper, tomato, tobacco, broccoli, cauliflower, cabbage, cowpea, canola, bean, soybean, rice, corn, wheat, barley, citrus, cotton, cassava, grape and walnut.

SEQUENCE LISTING

Figure 1:
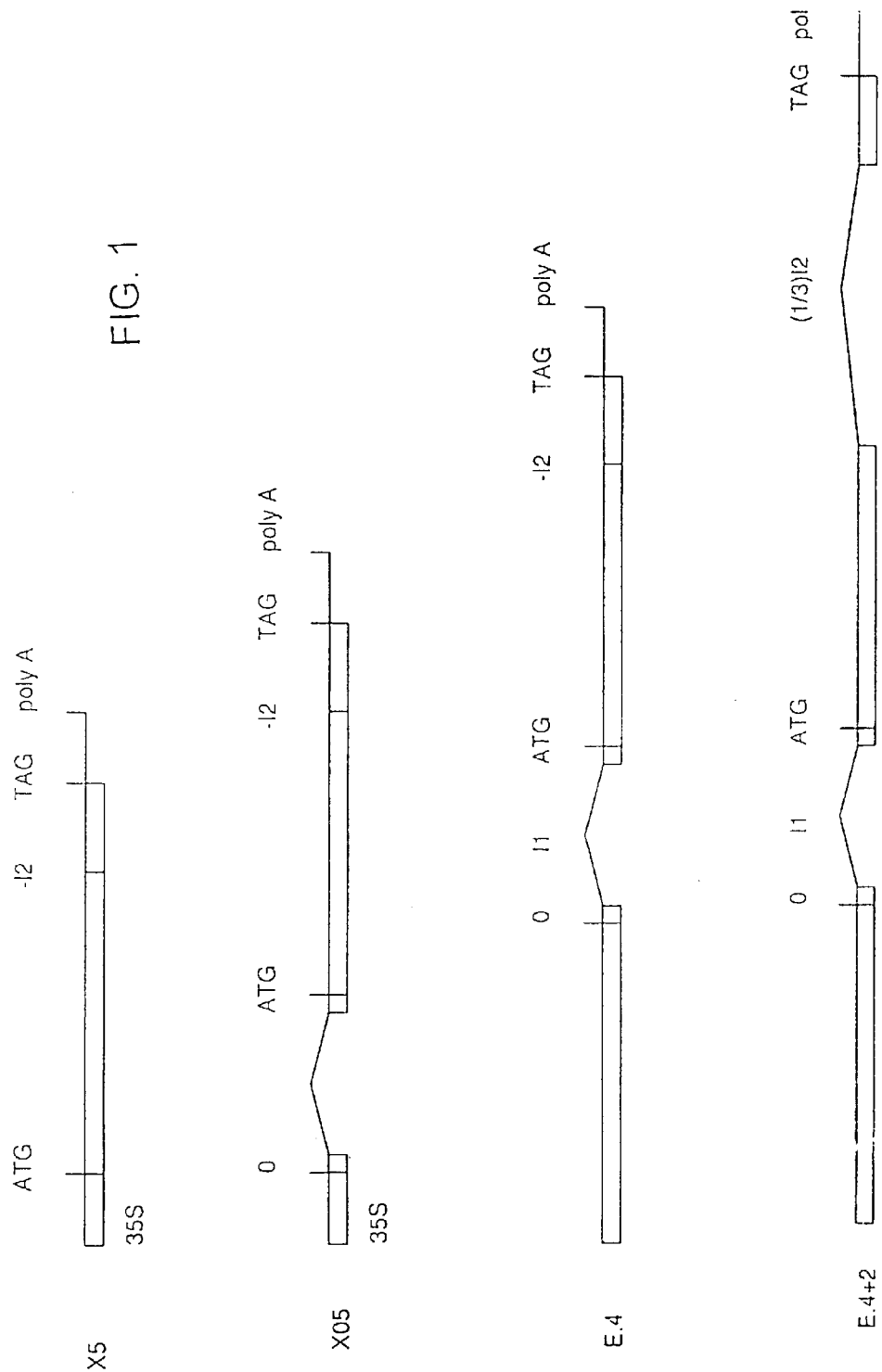
FIG. 1 is a schematic illustration of constructs introduced into plants in either the transient HR assay, or for stable transformation.

The nucleic and amino acid sequences listed in the accompanying sequence listing are showed using standard letter abbreviations for nucleotide bases, and three letter code for amino acids. Only one strand of each nucleic acid sequence is shown, but the complementary strand is understood as included by any reference to the displayed strand.

Seq. ID No. 1 shows the nucleic acid sequence of the pepper Bs2 gene. The sequence comprises the following regions:

| Nucleotides | Feature |
|---|---|
| 1–502 | promoter region |
| 503–554 | exon 1 (5' untranslated region (UTR)) |
| 555–1439 | intron 1 |
| 1440–1479 | exon 2 (5' UTR (continued)) |
| 1480–4162 | exon 2 continued (initiating ATG at 1480) |
| 4163–31184 | intron2 |
| 31185–31216 | exon 3 |
| 31217–31219 | stop codon |
| 31219–end | 3' UTR and 3' regulatory region |

Seq. ID No. 2 shows the nucleic acid sequence of the pepper Bs2 cDNA.

Seq. ID No. 3 shows the amino acid sequence of the pepper Bs2 protein.

Seq. ID No. 4 shows the nucleic acid sequence of the pepper Bs2 open reading frame (ORF).

Seq. ID Nos. 5–8 show primers that may be used to amplify certain portions of the pepper Bs2 cDNA.

Seq. ID No. 9 shows the nucleic acid sequence of the pepper Bs2 promoter.

DETAILED DESCRIPTION OF THE INVENTION

I. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

Bs2 protein biological activity: At a minimum, Bs2 protein biological activity refers to the ability of a protein to trigger HR when co-expressed in a plant with the gene product of AvrBs2 as determined by the transient assay described below. Bs2 protein biological activity may also confer resistance to *Xanthomonas campestris* ("Xc") when expressed in a plant or a plant cell that would otherwise be susceptible to Xc infection. This resistance activity may readily be determined by challenging Bs2-expressing transgenic plants with Xc, as described below.

Bs2 protein: A protein having Bs2 protein biological activity and sharing amino acid sequence identity with the amino acid sequence of the prototypical Bs2 protein shown in Seq. ID No. 3 (the pepper Bs2 protein). Bs2 proteins that are more distantly related to the prototypical Bs2 protein will share at least 50% amino acid sequence identity with the sequence shown in Seq. ID No. 3, as determined by the methods described below. More closely related Bs2 proteins may share at least 60%, 65%, 70%, 75% or 80% sequence identity with the pepper Bs2 protein. Bs2 proteins that are most closely related to the pepper protein will have Bs2 protein biological activity and share at least 85%, 90% or 95% sequence identity with the pepper protein.

Bs2 gene/Bs2 cDNA: Nucleic acid molecules that encode a Bs2 protein. Nucleic acid molecules that encode the pepper Bs2 protein are provided in Seq. ID No. 1 (pepper Bs2 gene), Seq. ID No. 2 (pepper Bs2 cDNA) and Seq. ID No. 4 (pepper Bs2 ORF). The invention includes not only the nucleic acid molecules provided in Seq. ID Nos. 1, 2 and 4, but also homologs and orthologs of these sequences, nucleic acid molecules that encode Bs2 proteins, and probes and primers that are derived from these sequences.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the pepper Bs2 cDNA or gene will anneal to a target sequence such as a Bs2 gene homolog from tomato contained within a tomato genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of the pepper Bs2 cDNA or gene sequences.

The invention thus includes isolated nucleic acid molecules that comprise specified lengths of the disclosed Bs2 cDNA or gene sequences. Such molecules may comprise at least 20, 25, 30, 35, 40 or 50 consecutive nucleotides of these sequences and may be obtained from any region of the disclosed sequences. By way of example, the pepper Bs2 cDNA and gene sequences may be apportioned into halves or quarters based on sequence length, and the isolated nucleic acid molecules may be derived from the first or second halves of the molecules, or any of the four quarters. The pepper Bs2 cDNA, shown in Seq. ID No. 2 may be used to illustrate this. The pepper Bs2 cDNA is 3099 nucleotides in length and so may be hypothetically divided into halves (nucleotides 1–1550 and 1551–3099) or quarters (nucleotides 1–775, 776–1550, 1551–2326 and 2327–3099). Nucleic acid molecules may be selected that comprise at least 20, 25, 30, 35, 40 or 50 consecutive nucleotides of any of these portions of the pepper cDNA. Thus, one such nucleic acid molecule might comprise at least 25 consecutive nucleotides of the region comprising nucleotides 1–1550 of the disclosed pepper cDNA.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the pepper Bs2 protein will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang el al. (1992); and Pearson et al. (1994). Altschul et al. (1994) presents a detailed consideration of sequence alignment methods and homology calculations.

The NCBI Basic Local Alignment Search Tool (BLAST) (Altschul et al)., 1990) is available from several sources, including the National Center for Biotechnology Information (NCBI, Bethesda, MID) and on the Internet, for use in connection with the sequence analysis programs blastp, blastn, blastx, tblastn and tblastx.

Orthologs of the disclosed pepper Bs2 protein are typically characterized by possession of at least 50% sequence identity counted over the full length alignment with the amino acid sequence of pepper Bs2 using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided. The present invention provides not only the peptide homologs are described above, but also nucleic acid molecules that encode such homologs.

An alternative indication that two nucleic acid molecules are closely related is that the two molecules hybridize to each other under stringent conditions. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Nucleic acid molecules that hybridize under stringent conditions to the pepper Bs2 sequences will typically hybridize to a probe based on either the entire pepper Bs2 cDNA or selected portions of the cDNA under wash conditions of 0.2× SSC, 0.1% SDS at 65° C. A more detailed discussion of hybridization conditions is presented below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Specific binding agent: An agent that binds substantially only to a defined target. Thus a Bs2 protein specific binding agent binds substantially only the Bs2 protein. As used herein, the term "Bs2 protein specific binding agent" includes anti-Bs2 protein antibodies and other agents that bind substantially only to the Bs2 protein.

Anti-Bs2 protein antibodies may be produced using standard procedures described in a number of texts, including Harlow and Lane (1988). The determination that a particular agent binds substantially only to the Bs2 protein may readily be made by using or adapting routine procedures. One suitable in vitro assay makes use of the Western blotting procedure (described in many standard texts, including Harlow and Lane (1988)). Western blotting may be used to determine that a given Bs2 protein binding agent, such as an anti-Bs2 protein monoclonal antibody, binds substantially only to the Bs2 protein.

Oligonucleotide: A linear polynucleotide sequence of up to about 100 nucleotide bases in length.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified Bs2 protein preparation is one in which the Bs2 protein is more enriched than the protein is in its natural environment within a cell. Generally, a preparation of Bs2 protein is purified such that the Bs2 represents at least 50% of the total protein content of the preparation. For particular applications, higher purity may be desired, such that preparations in which Bs2 represents at least 75% or at least 90% of the total protein content may be employed.

Ortholog: Two nucleotide or amino acid sequences are orthologs of each other if they share a common ancestral sequence and diverged when a species carrying that ancestral sequence split into two species. Orthologous sequences are also homologous sequences.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

II. Bs2 Protein and Nucleic acid Sequences

This invention provides Bs2 proteins and Bs2 nucleic acid sequences, including cDNA and gene sequences. The prototypical Bs2 sequences are the pepper sequences, and the invention provides for the use of these sequences to produce transgenic plants, such as pepper and tomato plants, having enhanced resistance to diseases cause by *Xanthomonas campestris*, such as bacterial spot disease. Because Xc causes disease in many plant species, and because the avirulence gene (AvrBs2) corresponding to Bs2 is found in many Xc pathovars, Bs2 will be useful to produce enhanced bacterial disease resistance in a wide variety of plant types.

A. Pepper Bs2

The pepper Bs2 gene sequence is shown in Seq. ID No. 1. The sequence comprises 2 introns and 3 exons. Intron 1 is located within the 5' untranslated region of the gene, hence exon 1 contains only 5' untranslated sequence. Intron 2 is very large (around 27 kb) and is located at the 3' end of the coding region. While the open reading frame continues across the 5' splice site of intron 2, resulting in a possible open reading frame encoding a hypothetical protein of 918 amino acids, no evidence has been found to suggest that this coding frame is actually utilized. Rather, only products in which intron 2 is spliced out are detected; splicing out intron 2 produces an open reading frame of 905 amino acids. This open reading frame is shown in Seq. ID No. 4, and the protein it encodes is shown in Seq. ID No. 3. A cDNA molecule corresponding to the spliced MRNA is shown in Seq. ID No. 2.

The pepper Bs2 protein includes a nucleotide binding motif and leucine rich repeats of the type that have been observed in other plant R genes (Leister et al., 1996, Aarts et al., 1998). As described in Examples 2 and 3 below, the pepper Bs2 protein has Bs2 biological activity, i.e., it mediates an AvrBs2-specific HR as determined by the Agrobacterium transient expression assay, and it produces a hypersensitive response following challenge of Bs2-expressing transgenic plants with Xc.

With the provision herein of the pepper Bs2 cDNA and gene sequences, the polymerase chain reaction (PCR) may now be utilized in a preferred method for producing nucleic acid sequences encoding the pepper Bs2 protein. For example, PCR amplification of the pepper Bs2 cDNA sequence may be accomplished either by direct PCR from a plant cDNA library or by Reverse-Transcription PCR (RT-PCR) using RNA extracted from plant cells as a template. Bs2 gene sequences may be amplified from plant genomic libraries, or plant genomic DNA. Methods and conditions for both direct PCR and RT-PCR are known in the art and are described in Innis et al. (1990). Suitable plant libraries for direct PCR include the pepper YAC library described by Tai et al. (1995).

The selection of PCR primers will be made according to the portions of the cDNA (or gene) that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al. (1990), Sambrook et al. (1989), and Ausubel et al (1992). By way of example only, the pepper Bs2 cDNA molecule as shown in Seq. ID No. 2 (excluding the poly A tail) may be amplified using the following combination of primers:

primer 1 5' CAAATATTTCTTGGAGTGAATTTGA 3' (Seq. ID No. 5)
primer 2 5' AAAACTAAACTGGTTGTCTCATCGT 3' (Seq. ID No. 6)

The open reading frame portion of the cDNA may be amplified using the following primer pair:

primer 3 5' ATGGCTCATGCAAGTGTGGCTTCTC 3' (Seq. ID No. 7)
primer 4 5' CTAATGTTCTTCTGAATCAGAATCA 3' (Seq. ID No. 8)

These primers are illustrative only; it will be appreciated by one skilled in the art that many different primers may be derived from the provided cDNA and gene sequences in order to amplify particular regions of these molecules. Resequencing of PCR products obtained by these amplification procedures is recommended; this will facilitate confirmation of the amplified sequence and will also provide information on natural variation on this sequence in different ecotypes and plant populations. Oligonucleotides derived from the pepper sequence may be used in such sequencing methods.

Oligonucleotides that are derived from the pepper Bs2 cDNA or gene sequences are encompassed within the scope of the present invention. Preferably, such oligonucleotide primers will comprise a sequence of at least 15–20 consecutive nucleotides of the pepper Bs2 cDNA or gene sequences. To enhance amplification specificity, oligonucleotide primers comprising at least 25, 30, 35, 40, 45 or 50 consecutive nucleotides of these sequences may also be used.

B. Bs2 Genes in Other Plant Species

Orthologs of the Bs2 gene are present in a number of plant species including tomato and tobacco (see Example 4 below). With the provision herein of the prototypical Bs2 protein from pepper and cDNA and gene sequences that encode this protein, the cloning by standard methods of cDNAs and genes that encode Bs2 protein orthologs in other plant species is now enabled. As described above, orthologs of the disclosed pepper Bs2 protein have Bs2 protein biological activity and are typically characterized by possession of at least 50% sequence identity counted over the full length alignment with the amino acid sequence of pepper Bs2 using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity.

Both conventional hybridization and PCR amplification procedures may be utilized to clone sequences encoding Bs2 protein orthologs. Common to both of these techniques is the hybridization of probes or primers derive from the pepper Bs2 cDNA or gene sequence to a target nucleotide preparation, which may be, in the case of conventional hybridization approaches, a cDNA or genomic library or, in the case of PCR amplification, a cDNA or genomic library, or an mRNA preparation.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the pepper Bs2 cDNA or gene. One of skill in the art will appreciate that sequence differences between the pepper Bs2 cDNA or gene and the target nucleic acid to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

For conventional hybridization techniques the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the pepper cDNA or gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Orthologs of the pepper Bs2 may alternatively be obtained by immunoscreening of an expression library. With the provision herein of the disclosed pepper Bs2 nucleic acid sequences, the enzyme may be expressed and purified in a heterologous expression system (e.g., $E.\ coli$) and used to, raise antibodies (monoclonal or polyclonal) specific for the pepper Bs2 protein. Antibodies may also be raised against synthetic peptides derived from the pepper Bs2 amino acid sequence presented herein. Methods of raising antibodies are well known in the art and are described in Harlow and Lane (1988). Such antibodies can then be used to screen an expression cDNA library produced from the plant from which it is desired to clone the Bs2 ortholog, using routine methods. The selected cDNAs can be confirmed by sequencing and enzyme activity.

C. Bs2 Sequence Variants

With the provision of the pepper Bs2 protein and Bs2 cDNA and gene sequences herein, the creation of variants of these sequences is now enabled.

Variant Bs2 proteins include proteins that differ in amino acid sequence from the pepper Bs2 sequence disclosed but which retain Bs2 protein biological activity. Such proteins may be produced by manipulating the nucleotide sequence of the pepper Bs2 cDNA or gene using standard procedures such as site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 1 shows amino acids which may be substituted for an original amino acid in a protein and which are regarded as conservative substitutions.

TABLE 1

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in enzymatic function or other features may be obtained by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed for Bs2 protein derivatives by analyzing the ability of the derivative proteins to confer Xc resistance in the assays described below.

Variant Bs2 cDNA or genes may be produced by standard DNA mutagenesis techniques, for example, M13 primer mutagenesis. Details of these techniques are provided in Sambrook et al. (1989), Ch. 15. By the use of such techniques, variants may be created which differ in minor ways, from the pepper Bs2 cDNA or gene sequences disclosed, yet which still encode a protein having Bs2 protein biological activity. DNA molecules and nucleotide sequences which are derivatives of those specifically disclosed herein and which differ from those disclosed by the deletion, addition or substitution of nucleotides while still encoding a protein that has Bs2 protein biological activity are comprehended by this invention. In their simplest form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence in such a way that, while the nucleotide sequence is substantially altered, it nevertheless encodes a protein having an amino acid sequence identical or substantially similar to the disclosed pepper Bs2 protein sequence. For example, the second amino acid residue of the pepper Bs2 protein is alanine. This is encoded in the pepper Bs2 open reading frame (ORF) by the nucleotide codon triplet GCT. Because of the degeneracy of the genetic code, three other nucleoticle codon triplets—GCA, GCC and GCG—also code for alanine. Thus, the nucleotide sequence of the pepper Bs2 ORF could be changed at this position to any of these three codons without affecting the amino acid composition of the encoded protein or the characteristics of the protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences which encode a Bs2 protein but which vary from the disclosed nucleic acid sequences by virtue of the degeneracy of the genetic code.

Variants of the Bs2 protein may also be defined in terms of their sequence identity with the prototype Bs2 protein shown in Seq. ID No. 3. As described above, Bs2 proteins have Bs2 biological activity and share at least 60% sequence identity with the pepper Bs2 protein. Nucleic acid sequences that encode such proteins may readily be determined simply by applying the genetic code to the amino acid sequence of a Bs2 protein, and such nucleic acid molecules may readily be produced by assembling oligonucleotides corresponding to portions of the sequence.

Nucleic acid molecules which are derived from the pepper Bs2 cDNA and gene sequences disclosed include molecules that hybridize under stringent conditions to the disclosed prototypical Bs2 nucleic acid molecules, or fragments thereof. Stringent hybridization conditions are hybridization at 65° C. in 6×SSC, 5×Denhardt's solution, 0.5% SDS and 100 μg sheared salmon testes DNA, followed by 15–30 minute sequential washes at 65° C. in 2×SSC, 0.1% SDS, followed by 1×SSC, 0.1% SDS and finally 0.2×SSC, 0.1% SDS.

Low stringency hybridization conditions (to detect less closely related homologs) are performed as described above but at 50° C. (both hybridization and wash conditions); however, depending on the strength of the detected signal, the wash steps may be terminated after the first 2×SSC, 0.1% SDS wash.

The pepper Bs2 gene or cDNA, and orthologs of these sequences from other plants, may be incorporated into transformation vectors and introduced into plants to produce enhanced disease resistance in such plants, as described in Example three below.

III. Introducing Bs2 into Plants

Once a cDNA (or gene) encoding a protein involved in the determination of a particular plant characteristic has been isolated, standard techniques may be used to express the cDNA in transgenic plants in order to modify that particular plant characteristic. The basic approach is to clone the cDNA into a transformation vector, such that it is operably linked to control sequences (e.g., a promoter) that direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector which integrates into the plant cell and which contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology, include:

U.S. Pat. No. 5,571,706 ("Plant Virus Resistance Gene and Methods");

U.S. Pat. No. 5,677,175 ("Plant Pathogen Induced Proteins");

U.S. Pat. No. 5,510,471 ("Chimeric Gene for the Transformation of Plants");

U.S. Pat. No. 5,750,386 ("Pathogen-Resistant Transgenic Plants");

U.S. Pat. No. 5,597,945 ("Plants Genetically Enhanced for Disease Resistance");

U.S. Pat. No. 5,589,615 ("Process for the Production of Transgenic Plants with Increased Nutritional Value Via the Expression of Modified 2S Storage Albumins");

U.S. Pat. No. 5,750,871 ("Transformation and Foreign Gene Expression in Brassica Species");

U.S. Pat. No. 5,268,526 ("Overexpression of Phytochrome in Transgenic Plants");

U.S. Pat. No. 5,262,316 ("Genetically Transformed Pepper Plants and Methods for their Production"); and U.S. Pat. No. 5,569,831 ("Transgenic Tomato Plants with Altered Polygalacturonase Isoforms").

These examples include descriptions of transformation vector selection, transformation techniques and the construction of constructs designed to over-express the introduced cDNA. In light of the foregoing and the provision herein of the Bs2 cDNA and gene sequences, it is thus apparent that one of skill in the art will be able to introduce these nucleic acids, or homologous or derivative forms of these molecules, into plants in order to produce plants having enhanced Bs2 activity. Expression of Bs2 in plants that are otherwise sensitive to certain bacterial diseases, such as bacterial spot diseases, will be useful to confer enhanced resistance to these diseases. Expression of a Bs2 transgene in plants that already express Bs2 protein may be used to further boost pathogen resistance.

A. Plant Types

Bacterial diseases affect many plant species, and in particular, *Xanthomonas campestris* can infect a wide variety of plants. At the molecular level, not only are orthologs of Bs2 found in a number of plant species, but the avrBs2 gene is found in a wide variety of Xc pathovars (Kearney & Staskawicz, 1990) that cause disease in many different plants including tomato, pepper, rice, citrus, cowpea, walnut, brassica (broccoli, cauliflower, cabbage), soybean, bean, alfalfa and grapes. Thus, the Bs2 protein may be usefully expressed in a wide range of higher plants to confer enhanced resistance to bacterial disease, both monocotyledonous and dicotyledenous plants, including, but not limited to maize, wheat, rice, barley, soybean, cotton, beans in general, rape/canola, alfalfa, flax, sunflower, safflower, brassica, cotton, tobacco, flax, peanut, clover, cowpea, grapes; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; and flowers such as carnations and roses.

B. Vector Construction, Choice of Promoters

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters that may be useful for expressing the cDNA include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua. 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of the cDNA in plant cells, including promoters regulated by: (a) heat (Callis et al., 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones, such as abscisic acid (Marcotte et al., 1989); (d) wounding (e.g., wunl, Siebertz et al., 1989); and (e) chemicals such as methyl jasminate or salicylic acid (see also Gatz et al., 1997).

Alternatively, tissue specific (root, leaf, flower, and seed for example) promoters (Carpenter et al. 1992, Denis et al. 1993, Opperman et al. 1993, Stockhause et al. 1997; Roshal et al., 1987; Schernthaner et al., 1988; and Bustos et al., 1989) can be fused to the coding sequence to obtained particular expression in respective organs.

Alternatively, the native Bs2 gene promoter may be utilized. The Bs2 gene promoter is contained within the ca. 2 kb sequence shown in Seq. ID No. 9. The 3' end of this sequence ends at the transcriptional start site for the Bs2 gene (equivalent to nucleoticle number 503 in Seq. ID No. 1). One of skill in the art will appreciate that less than this entire sequence may be used in order to obtain effective promoter activity. The determination of whether a particular region of this sequence confers effective promoter activity may readily be ascertained by operably linking the selected sequence region to the Bs2 cDNA (in conjunction with suitable 3' regulatory region, such as the NOS 3' regulatory region as discussed below) and determining whether the resulting construct is able to elicit HR response in the transient assay described below. Promoter regions that comprise, for example, nucleotides 250–2053, 500–2053, 1000–2053 or 1500–2053 of Seq. ID No. 9 may readily be employed.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions. The Bs2 gene 3' regulatory sequence may also be employed.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

C. Arrangement of Bs2 Sequence in Vector

The particular arrangement of the Bs2 sequence in the transformation vector will be selected according to the type of expression of the sequence that is desired.

In most instances, enhanced Bs2 activity is desired, and the Bs2 ORF is operably linked to a constitutive high-level promoter such as the CaMV 35S promoter. As noted above, enhanced Bs2 activity may also be achieved by introducing into a plant a transformation vector containing a variant form of the Bs2 cDNA or gene, for example a form which varies from the exact nucleotide sequence of the Bs2 ORF, but which encodes a protein that retains Bs2 biological activity.

D. Transformation and Regeneration Techniques

Transformation and regeneration of both monocotyledonous and dicotyledonous plant cells is now routine, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

E. Selection of Transformed Plants

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to determine whether the susceptibility of the plant to Xc infection has been altered as a result of the introduced transgene.

IV. Production of Recombinant Bs2 Protein in Heterologous Expression Systems

Many different expression systems are available for expressing cloned nucleic acid molecules. Examples of prokaryotic and eukaryotic expression systems that are routinely used in laboratories are described in Chapters 16–17 of Sambrook et al. (1989). Such systems may be used to express Bs2 at high levels to facilitate purification of the protein. The purified Bs2 protein may be used for a variety of purposes. For example, the purified recombinant enzyme may be used as an immunogen to raise anti-Bs2 antibodies. Such antibodies are useful as both research reagents (such as in the study of phytopathogen defense mechanisms in plants) as well as diagnostically to determine expression levels of the protein in plants that are being developed for agricultural use. Thus, the antibodies may be used to quantify the level of Bs2 protein both in existing plant varieties and in transgenic varieties that are designed to over-express the Bs2 protein. Such quantification may be performed using standard immunoassay techniques, such as ELISA and in situ immunofluorescence and others described in Harlow & Lane (1988).

By way of example only, high level expression of the Bs2 protein may be achieved by cloning and expressing the Bs2 cDNA in yeast cells using the pYES2 yeast expression vector (Invitrogen, Carlsbad, Calif.). Alternatively, a genetic construct may be produced to direct secretion of the recombinant Bs2 protein from the yeast cells into the medium. This approach will facilitate the purification of the Bs2 protein, if this is necessary. Secretion of the recombinant protein from the yeast cells may be achieved by placing a yeast signal sequence adjacent to the Bs2 coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985).

Alternatively, the enzyme may be expressed at high level in prokaryotic expression systems, such as *E. coli*, as described in Sambrook et al. (1989). Commercially available prokaryotic expression systems include the pBAD expression system and the ThioFusion expression system (Invitrogen, Carlsbad, Calif.).

EXAMPLES

Example 1

Cloning Pepper Bs2

The Bs2 gene was isolated by positional cloning. Molecular markers tightly linked to the Bs2 gene were identified by randomly amplified polymorphic DNA (RAPD) and amplified fragment length polymorphism (AFLP) analysis and a high resolution genetic map of the locus was constructed. The closest markers were used to screen a yeast artificial chromosome (YAC) library of a pepper cultivar containing the Bs2 gene and two clones spanning the locus were identified (i.e. chromosome landing). Further high resolution mapping facilitated the physical delimitation of the locus to a region of approximately 103 kb which was completely sequenced. The Bs2 gene was identified by testing candidates (of which there were only two) using the Agrobacterium-mediated transient assay described below.

Example 2

Transient Expression Assay for Bs2

To test Bs2 candidates for functional activity, an Agrobacterium-mediated transient transformation assay was used. Constructs for expression in the Agrobacterium-mediated transient assay were made using the pMD 1 binary expression vector. The pMB1 vector is a derivative of pBI121 (Clontech, Palo Alto, Calif.) in which the GUS reporter gene has been replaced with a synthetic polylinker (M. Dixon, unpublished). The pDD5 construct consists of the avrBs2 orf (Swords et al. 1996) cloned between the 35S promoter and the NOS terminator sequences of pMD1. This construct was mobilized into *A. tumefaciens* strain C58C1 (pCH32) using standard methods. The pCH32 plasmid contains the VirE and VirG genes (A. Hamilton, unpublished) and was constructed by cloning the VirE operon from pSW108 (Winans et al., 1987) into the PvuII site of pCH30 (a derivative of the pCC 113 (Chen et al., 1991). Cells containing the construct were grown in a 5 ml L-broth culture containing antibiotics (tetracycline 5 μg/ml and kanamycin 50 μg/ml) overnight. This culture was used to inoculate a 50 ml L-broth culture containing antibiotics (tetracycline 5 μg/ml and kanamycin 50 μg/ml), 10 mM MES, and 20 μM acetosyringone. Following overnight growth, bacteria were collected by centrifugation and resuspended in 10 mM MgCl2, 10 mM MES, and 150 μM acetosyringone to a final OD$_{600}$ Of 0.6. After 2–3 hours, about 10 μl of the cells were hand-infiltrated into intercellular leaf spaces of pepper cultivars with and without the Bs2 resistance gene using a plastic transfer pipet (a modification of the method described by Minsavage et al., 1990). After 24 hours, a characteristic macroscopic hypersensitive response comprising browning of tissue and necrosis in the infiltrated area (HR, Minsavage et al. 1990) was observed only in pepper plants containing the Bs2 resistance gene. No macroscopic reaction was observed in the pepper plants lacking the Bs2 gene. These results show that the transient assay system is able to elicit a detectable HR response when the Bs2 and avrBs2 genes are simultaneously expressed in the same cells of the pepper plant.

A variation on this assay was then utilized to asses the ability of various forms of the Bs2 gene to trigger HR response. This assay is essentially performed by co-infiltrating leaves of susceptible plants with two Agrobacterium clones, one containing avrBs2, the other containing the Bs2 construct. HR response is typically manifested within 48 hours as browning and necrosis within the area of infiltration.

Four constructs comprising various forms of the Bs2 gene were produced. The constructs, as depicted in FIG. 1 comprise: the Bs2 cDNA operably linked to 35S promoter and the NOS 3' regulatory region (construct X5); the same construct having intron 1 inserted at the position that the intron occurs in the Bs2 gene (construct XO5); a construct that is identical to construct XpMD1 O5 except that the 35S promoter is replaced with the native Bs2 promoter (shown in Seq. ID No. 9) (construct E.4). Construct E.4+2 comprises the Bs2 gene (including the Bs2 promoter and 3' regulatory regions) with a truncated form of intron 2 of Bs2.

To make these transient expression constructs using the Bs2 gene, adapter primers containg an XbaI site were designed for PCR amplification of the 5' end of ther Bs2 gene. For the X5 construct, the primer was 5' CCTCTA-GATGGCTCATGCAAGTGTGCGTTCTCTTATG 3' (underlined sequence is the XbaI site, bolded sequence encodes the first 10 amino acids of Bs2). For the XO5 construct which includes the first intron located in the 5' UTR sequence, the primer was 5'CCTCTAGA-CAAAATATTTCTTGGAGTGAATTTGA 3' (underlined sequence is the XbaIsite, bolded letter is the transcriptional start site of the Bs2). For both constructs the second primer used for amplification was 5' CCATCCCACACTTCA-CAACTCCA 3'. Amplified products were cloned and sequenced to check fidelity of the clones. Clones for both constructs were digested with XbaI and SalI and ligated to pMD1 vector that had been digested with XbaI and SalI. The majority of the Bs2 was isolated as a SalI-EcoRI fragment from a cosmid that was cloned into pBluescript KS+ (Stratagene, La Jolla, Calif.). The 3' ends of the two constructs were derived from PCR amplification of the appropriate 3' RACE product using the primers 5' GTCCTTGAGCGCCTCATG 3' and 5' ACTAAACTGGGT-GTCTCATCGT 3'. This PCR products was cloned into the pCRII-TOPO vector (Invitrogen, Carlsbad, Calif.) and sequenced to check the fidelity of the clone. The 3' end fragment was isolated by digesting th pCRII-TOPO clone with EcoRI and ligating the fragment to the SalI-EcoRI pBluescript KS+construct that had been digested with EcoRI. Proper orientation of the Eco RI 3' end fragment was determined by sequencing. This construct was digested with SalI and SacI (the SacIsite is in the plasmid polylinker) and ligated to the initial pMD1 constructs which has been digested with SalI and SacI, to produce the X5 an XO5 constructs.

Transient assay constructs (E.4 and E.4+2) to examine the native promoter region of the Bs2 were made by digesting a clone of the cosmid contig spanning the Bs2 locus with DraIII which cuts approximately 2050 bp upstream of the transcriptional start site. Following digestion, T4 DNA polymerase was used to fill in the DraIII end and digestion with EcoRI was performed. This resulted in the liberation of a fragment of approximately 5.6 kb (from the DraIII site to the EcoRI site located at position 2620 of the cDNA). This fragment was cloned into the binary cosmid vector pCLD04541 (Bent et al., 1994) which had been previously digested with XhoI, subjected to T4 DNA polymerase treatment and then digested with EcoRI. Ligation of the 5.6 kb fragment into the vector resulted in the elimination of the DraIII and XhoI sites. For construct E.4, the 3' end of Bs2 was isolated from the pCRII-TOPO clone by digestion with EcoRI as described for the construction of the X5 and XO5 constructs. This clone was ligated to the 5.6 kb pCLD04541 construct at the EcoRI site to yield the E.4 construct. Clones were sequenced to ensure proper orientation of the EcoRI fragment.

To obtain the E.4+2 construct, the E.4 construct was digested with XhoI (XhoI site al position 1784 of the cDNA, position 3263 of the genomic sequence) and SpeI (which cuts at the SpeI site in the vector polylinker) and this region was replaced with a XhoI-SpeI (position 3263 to 7539 of the Bs2 genomic sequence) fragment of about 4.3 kb isolated from a Bs2 cosmid clone. This intermediate construct was digested with XbaI which cuts a site about 2.5 kb past the start of intron 2 (position 6648 of the Bs2 genomic sequence) and a site in the pCLD04541 vector. The smaller XbaI fragment (containing 1.1 kb of intron 2 from position 6648 to 7539) was replaced with an XbaI fragment of about 3 kb containing part of the 3' end of intron 2 (about 1.2 kb) and the 3' end of the NBS-LRR candidate and regulatory elements located about 1.7 kb downstream of the end of the orf (XbaI site at position 29957 in Bs2 genomic sequence, end of intron 2 at position 31184, end of orf 31216).

Strains containing these constructs were grown as described above for the 35S-avrBs2 construct. Following resuspension in the final buffer, a volume of cells containing the candidate constructs were mixed with an equal volume of cells containing the 35S-avrBs2 construct. The resulting effective concentration of the cells was OD$_{600}$=0.3. These cells were then hand-infiltrated into the intercellular leaf space as described above. As controls, suspensions of cells with the 35S-avrBs2 construct only and suspensions of cells with the Bs2 constructs only were infiltrated in comparable areas of the same leaves. Three different plant species were used in this assay: susceptible pepper cultivar ECW (i.e. bs2/bs2), susceptible tomato cultivar Walter, and non-host *Nicotiana benthamiana*. HR responses were typically observed within 48 hours and varied depending on the construct and the host plant. The results are shown in Table 2 below.

TABLE 2

Agrobacterium-mediated transient transformation assay

| Construct | N. benthamiana | Pepper (ECW) | Tomato (Walter) |
|---|---|---|---|
| 35S-avrBs2 | – | – | – |
| X5 | – | – | – |
| XO5 | – | – | – |
| E.4 | – | – | – |
| E.4 + 2 | – | – | – |
| X5/35S-avrBs2 | ++++ | ++ | + |
| XO5/35S-avrBs2 | ++ | + | – |
| E.4/35S-avrBs2 | +/– | – | – |
| E.4 + 2/35S-avrBs2 | +/– | – | – |

Reactions were scored at 48 hours post-infiltration. Plants were grown under greenhouse conditions. Following infiltration, plants were placed in growth chamber under standard conditions during the length of the assay.

Scoring scale ++++ strong HR characterized by confluent necrosis of the area infiltrated/strong browning of collapsed tissue (typical of Xcv avrBs2lBs2 pepper reaction); ++ moderate HR characterized by necrosis over the entire infiltrated area, but not complete collapse of the area, tissue clearly showing browning; + weak HR some collapse in the area of infiltration, light browning of the area; – no HR, some wound associated browning localized to point of infiltration, but not to entire infiltrated area).

These results indicate that the introduction of Bs2 constructs into various species of susceptible plants is sufficient to trigger HR in the presence of AvrBs2.

Example 3
Stable Transformation of Bs2 into Plants

The X5, XO5, E.4 and E.4+2 constructs were stably transformed into pepper, tomato and tobacco varieties described above using standard procedures.

Analysis of the Xc resistance phenotypes of these transgenic plants is determined by challenging plants with Xcv by hand infiltration as described above for the Agrobacterium transient expression assay. HR is determined by visual inspection.

Example 4
Bs2 Homologs

As noted above, homologs of Bs2 exist in a number of plant species including pepper, tomato and tobacco. The existence of these sequences may be demonstrated by hybridization techniques, such as Southern blotting. Southern blotting using high stringency hybridization conditions reveals the presence of Bs2 homologs in pepper and tomato. Hybridization was performed using probes based on different portions of the Bs2 gene sequence. Probes were hybridized to tomato genomic DNA, and to genomic DNA from Xc pv. vesicatoria resistant and susceptible lines of Capsicum annuum. Hybridization was performed at 65° C. in 6×SSC, 5×Denhardt's solution, 0.5% SDS and 100 µg sheared salmon testes DNA, followed by 15–30 minute sequential washes at 65° C. in 2×SSC, 0.1% SDS, followed by 1×SSC, 0.1% SDS and finally 0.2×SSC, 0.1% SDS.

Under these conditions, a probe comprising nucleotides 1–927 of Seq. ID No. 1 (and 107 nucleotides 5' of this sequence, shown in Seq. ID No. 9) shows hybridization to a single band in the Xcv resistant pepper, and no hybridization to the Xcv susceptible pepper. A probe comprising nucleoticles 1042–2239 of Seq. ID No. 1 showed hybridization to approximately 15 bands in both resistant and susceptible pepper, and to a single band in tomato.

Lower stringency hybridization conditions are used to detect Bs2 homologs in less closely related species. For example, hybridization of either of these probes under low stringency hybridization conditions as described above is used to detect homologs from brassica and other plant species. Once a Bs2-hybridizing band is detected in a plant species, standard techniques such as screening cDNA or genomic libraries from the plant with the Bs2 probe may be used. Alternatively, Bs2 homologs may be isolated by screening an expression library from the plant in question using a Bs2 protein specific binding agent, such as an anti-Bs2 antibody produced as described above. Such homologs may be introduced into plants using the methods described above in order to produce enhanced resistance to Xc pathogens.

REFERENCES

Aarts et al. (1998) *Mol. Plant-Microbe Interact.* 11: 251–258.
Ainley et al. (1993) *Plant Mol. Biol.* 22: 13–23.
Altschul & Gish. (1996). *Methods Enzymol.*, 266: 460–80.
Altschul et al. (1990). *J Mol. Biol.*, 215: 403–10
Altschul et al. (1994). *Nature Genet.*, 6: 119–29.
An et al. (1988) *Plant Physiol.* 88: 547.
Ausubel et al. (1987) In *Current Protocols in Molecular Biology*, Greene Publishing Associates and Wiley-Intersciences.
Bechtold et al. (1993) *C.R. Acad. Sci. Paris, Sciences de la vie/Life sciences* 316: 1194–1199.
Bent et al. (1994) *Science* 265: 1856–1860.
Benfey & Chua (1990) *Science* 250: 959–966.
Bustos et al. (1989) *Plant Cell* 1: 839.
Callis et al. (1988) *Plant Physiol.* 88: 965.
Carpenter et al. (1992) *The Plant Cell* 4: 557–571.
Chang et al. (1986) *Mol. And Cell. Biol.* 6: 1812–1819.
Chen et al. (1991) *Mol. Gen. Genet.* 230: 302.
Cook and Stall (1963) *Phytopathology* 53: 1060–1062.
Cook and Guevara (1984) *Plant Dis.* 68: 329–330.
Corpet et al. (1988). *Nucleic Acids Research* 16, 10881–90.
Dekeyser et al. (1990) *Plant Cell* 2: 591.
Denis et al. (1993) *"Expression of engineered nuclear male sterility in Brassica napus." Plant Physiol.* 101: 1295–1304.
Fromm et al. (1989) *Plant Cell* 1: 977.
Gan & Amansino (1995) *Science* 270: 1986–1988.
Gatz et al. (1997) *Ann. Rev. Plant Physiol. Plant Mol. Biol* . 48: 89–108.
Gelvin et al. (1990) *Plant Molecular Biology Manual*, Kluwer Academic Publishers.
Gilmartin et al. (1992) *The Plant Cell* 4: 839–949.
Harlow & Lane (1988) *Antibodies, A Laboratory Manual*, Cold Spring Harbor Laboratory, N.Y.
Herbers et al. (1992) *Nature* 356: 172–174.
Hibberd et al. (1987) *Phytopathology* 77: 1304–1307.
Higgins and Sharp (1988). *Gene* 73: 237–244.
Higgins and Sharp (1989). *CABIOS* 5: 151–153.
Huang, et al. (1992). *Computer Applications in the Biosciences* 8: 155–65.
Innis et al. (eds.) (1990) *PCR Protocols, A Guide to Methods and Applications*, Academic Press, Inc., San Diego, Calif.
Jones and Scott (1986) *Plant Dis.* 70: 337–339.
Kim and Hartman (1985) *Plant Dis.* 69: 233–235.
Kawasaki et al. (1990). In *PCR Protocols, A Guide to Methods and Applications*, Innis et al. (eds.), 21–27, Academic Press, Inc., San Diego, Calif.
Kearney et al. (1988) *Nature* 332: 541–543.
Kearney and Staskawicz (1990) *Nature* 346: 385–386.

Kuhlemeier et al. (1989) *Plant Cell* 1: 471.
Leister et al. (1996) *Nature Genetics* 14: 421–429.
Liang & Richardson (1993) *J. Agric. Food Chem.* 41: 1800–1807.
Marcotte et al. (1989) *Plant Cell* 1: 969.
Martin et al. (1993) *Science* 262: 1432–1436.
Minsavage et al. (1990) *Mol. Plant-Microbe Interact.* 3: 41–47.
Needleman and Wunsch (1970). *J. Mol. Biol.* 48: 443.
Odel et al. (1985) *Nature* 313: 810.
Odell et al. (1994) *Plant Physiol.* 106: 447–458.
Opperman et al. (1993) *Science* 263: 221–223.
Pearson and Lipman (1988). *Proc. Natl. Acad. Sci. USA* 85: 2444.
Pearson et al. (1994). *Methods in Molecular Biology* 24: 307–31.
Roshal et al. (1987) *EMBO J.* 6: 1155.
Sambrook et al. (1989) *In Molecular Cloning: A Laboratory Manual*, Cold Spring Harbor, N.Y.
Schafflier & Sheen (1991) *Plant Cell* 3: 997.
Schemthaner et al. (1988) *EMBO J.* 7: 1249.
Siebertz et al. (1989) *Plant Cell* 1: 961.
Smith et al. (1985) *Science* 229: 1219–1224.
Smith and Waterman (198 1). *Adv. Appl. Math.* 2: 482.
Stockhause et al. (1997) *The Plant Cell* 9: 479–489.
Swanson et al. (1988) *Mol. Plant-Microbe Interact.* 1: 5–9.
Swords et al. (1996) *J. Bacteriol.* 178: 4661–4669.
Tai (1995) Molecular Genetic Characterization of the Bs2 Resistance Locus in Pepper, Ph.D. Thesis, University of California, Berkeley.
Terada & Shimamoto (1990) *Mol. Gen. Genet.* 220: 389.
Tijssen (1993). *Laboratory Techniques in Biochemistry and Molecular Biology— Hybridization with Nucleic Acid Probes* Part 1, Chapter 2 "Overview of principles of hybridization and the strategy of nucleic acid probe assays", Elsevier, N.Y.
Van der Ackerveken et al. (1992) *Plant J.* 2: 359–366.
Weissbach & Weissbach (1989) *Methods for Plant Molecular Biology*, Academic Press.
Winans et al. (1987) *Nuc. Acids Res.* 15: 825

That which is claimed:

1. An isolated protein comprising the amino acid sequence set forth in SEQ ID NO: 3.

2. An isolated protein comprising an amino acid sequence having at least 85% sequence identity to the amino acid sequence set forth in SEQ ID NO: 3, wherein said protein comprises Bs2 protein biological activity.

3. An isolated protein encoded by a nucleic acid molecule comprising a nucleotide sequence selected from the group consisting of:

(a) the nucleotide sequence set forth in SEQ ID NO: 1;
(b) the nucleotide sequence set forth in SEQ ID NO: 2; and
(c) the nucleotide sequence set forth in SEQ ID NO: 4.

4. An isolated protein comprising an amino acid sequence having at least 95% sequence identity to the amino acid sequence set forth in SEQ ID NO: 3, wherein said protein comprises Bs2 protein biological activity.

* * * * *

UNITED STATES PATENT AND TRADEMARK OFFICE
CERTIFICATE OF CORRECTION

PATENT NO. : 6,762,285 B2
DATED : July 13, 2004
INVENTOR(S) : Staskawicz et al.

It is certified that error appears in the above-identified patent and that said Letters Patent is hereby corrected as shown below:

Column 67,
Lines 4-7, delete Claim 2.

Signed and Sealed this

Twenty-third Day of November, 2004

JON W. DUDAS
*Director of the United States Patent and Trademark Office*